United States Patent
Lin et al.

(10) Patent No.: US 9,783,811 B2
(45) Date of Patent: *Oct. 10, 2017

(54) INDUCIBLE GENE EXPRESSION COMPOSITION FOR USING EUKARYOTIC POL-2 PROMOTER-DRIVEN TRANSCRIPTION IN PROKARYOTES AND THE APPLICATIONS THEREOF

(71) Applicant: MELLO BIOTECHNOLOGY, INC., Santa Fe Springs, CA (US)

(72) Inventors: Shi-Lung Lin, Arcadia, CA (US); Donald C. Chang, Cerritos, CA (US)

(73) Assignee: MELLO BIOTECHNOLOGY, INC., Santa Fe Springs, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/502,608

(22) Filed: Sep. 30, 2014

(65) Prior Publication Data

US 2015/0064771 A1    Mar. 5, 2015

Related U.S. Application Data

(62) Division of application No. 13/572,263, filed on Aug. 10, 2012, now abandoned.

(60) Provisional application No. 61/522,843, filed on Aug. 12, 2011.

(51) Int. Cl.
| | |
|---|---|
| C12N 15/74 | (2006.01) |
| C12P 21/06 | (2006.01) |
| C12N 15/63 | (2006.01) |
| C12N 1/38 | (2006.01) |
| C12N 15/70 | (2006.01) |
| A01K 67/00 | (2006.01) |

(52) U.S. Cl.
CPC ............ *C12N 15/635* (2013.01); *C12N 1/38* (2013.01); *C12N 15/70* (2013.01)

(58) Field of Classification Search
CPC ......... C12N 15/635; C12N 1/38; C12N 15/70
See application file for complete search history.

(56) References Cited

U.S. PATENT DOCUMENTS

| | | | |
|---|---|---|---|
| 4,879,226 A | 11/1989 | Wallace et al. | |
| 5,464,758 A | 11/1995 | Gossen et al. | |
| 6,251,599 B1 | 6/2001 | Chen | |
| 7,064,186 B2* | 6/2006 | Sprecher ............... | A61K 38/00 435/69.5 |
| 7,959,926 B2 | 6/2011 | Buechler et al. | |
| 7,968,311 B2 | 6/2011 | Mehta et al. | |
| 2005/0019808 A1* | 1/2005 | Palmenberg ......... | C07K 14/005 435/5 |
| 2007/0099277 A1 | 5/2007 | Anderson et al. | |
| 2008/0057034 A1* | 3/2008 | Hassan ............... | A61K 39/0258 424/93.2 |
| 2008/0293143 A1* | 11/2008 | Lin ........................ | C12N 15/63 435/456 |
| 2009/0203141 A1 | 8/2009 | Lin et al. | |
| 2010/0240126 A1 | 9/2010 | Lin et al. | |
| 2010/0272758 A1* | 10/2010 | Woodard ........... | A61K 39/0258 424/249.1 |
| 2011/0159552 A1* | 6/2011 | Masuda ............... | A61K 31/713 435/91.32 |
| 2011/0165680 A1* | 7/2011 | Blattner ................. | C12N 15/79 435/454 |

FOREIGN PATENT DOCUMENTS

WO    WO02/24904    *    3/2002

OTHER PUBLICATIONS

Lewin et al. Viral promoters can initiate expression of toxin genes introduced into *Escherichia coli*. BMC Biotechnology 2005, 5:19 doi:10.1186/1472-6750-5-19, pp. 1-9.*
Neidhardt et al. Culture medium for enterobacteria. J. Bacteriology 119:736-747, 1974.*
Zhou et al. An RNA polymerase II construct synthesizes short-hairpin RNA with a quantitative indicator and mediates highly efficient RNAi. Nucleic Acids Res. 33: e62 doi:10.1093/nar/gni061, pp. 1-8, 2005.*
Colón-González et al., "Anaerobic Growth does not Support Biofilm Formation in *Escherichia coli* K-12", Research in Microbiology, vol. 155 (2004) pp. 514-521.
Pantanella et al., "Violacein and Biofilm Production in *Janthinobacterium Lividum*", Journal of Applied Microbiology, vol. 102 (2007) pp. 992-999.
Gao et al., "Aminated Linear and Star-Shape Poly(glycerol methacrylate)s: Synthesis and Self-Assembling Properties", Biomacromolecules, vol. 11 (2010) pp. 889-895.
Gossen et al., "Tight control of gene expression in mammalian cells by tetracycline-responsive promoters", Proceedings of the National Academy of Science, USA., vol. 89, Jun. 1992, pp. 5547-5551.

(Continued)

*Primary Examiner* — Quang Nguyen
(74) *Attorney, Agent, or Firm* — Birch, Stewart, Kolasch & Birch, LLP

(57) ABSTRACT

Eukaryotic protein-coding messenger RNAs and non-coding microRNAs are naturally transcribed by type II RNA polymerases (pol-2) but not prokaryotic RNA polymerases. As a result, current eukaryotic RNA and protein production is performed either using eukaryotic pol-2 promoters in hybridomas or mammalian cells or using prokaryotic promoters in bacterial cells. However, because prokaryotic RNA transcription tends to be error-prone, frequent mutation is a big problem. Also, growing hybridomas or mammalian cells is relatively laborious and costly. To overcome these problems, the present invention provides a novel inducible composition and method for producing eukaryotic RNAs and/or their related peptides/proteins directly using eukaryotic pol-2 promoter-driven gene expression in fast growing bacteria, without the need of changing to prokaryotic promoters or growing hybridomas/mammalian cells. The RNAs and peptides/proteins so obtained can be used to develop drugs, cure diseases, treat tumors/cancers, produce pluripotent stem (iPS) cells, enhance wound healing, and make foods.

22 Claims, 11 Drawing Sheets
(7 of 11 Drawing Sheet(s) Filed in Color)

(56) References Cited

OTHER PUBLICATIONS

Lin et al., "Gene silencing in vitro and in vivo using intronic microRNAs", Methods in Molecular Biology, vol. 342:MicroRNA Protocols, Edited by S. Ying, 2006, Humana Press, Totowa, New Jersey, pp. 295-312.

Lin et al., "Intron-mediated RNA interference and microRNA (miRNA)", Frontiers in Bioscience, vol. 13, Jan. 1, 2008, pp. 2216-2230.

Lin et al., "MicroRNA miR-302 inhibits the tumorigenecity of human pluripotent stem cells by coordinate suppression of CDK2 and CDK4/6 cell cycle pathways", Cancer Research, vol. 70, No. 22, Nov. 5, 2010, pp. 9473-9482.

Lin et al., "Mir-302 reprograms human skin cancer cells into a pluripoterl ES-cell-like state", RNA, vol. 14 (2008) pp. 2115-2124.

Lin et al., "Regulation of somatic cell reprogramming through inducible mir-302 expression", Nucleic Acids Research, vol. 39, No. 3 (2011) pp. 1054-1065.

Lin et al., "Role of mir-302 microRNA family in stem cell pluripotency and renewal", Edited by Ying Sy, Current Perspectives in MicroRNAs (miRNA), (2008) pp. 167-185.

Lin et al., "Transgene-like animal models using intronic microRNAs", Methods in Molecular Biology, vol. 342:MicroRNA Protocols, Edited by S. Ying, 2006, Humana Press, Totowa, New Jersey, pp. 321-334.

McDowell et al., "Determination of Intrinsic Transcription Termination Efficiency by RNA Polymerase Elongation Rate", Science, vol. 266 (1994) pp. 822-825.

Simonsson et al., "DNA demethylation is necessary for the epigenetic reprogramming of somatic cell nuclei", Nature Cell Biology, vol. 6, No. 1, Oct. 2004, pp. 984-990.

* cited by examiner

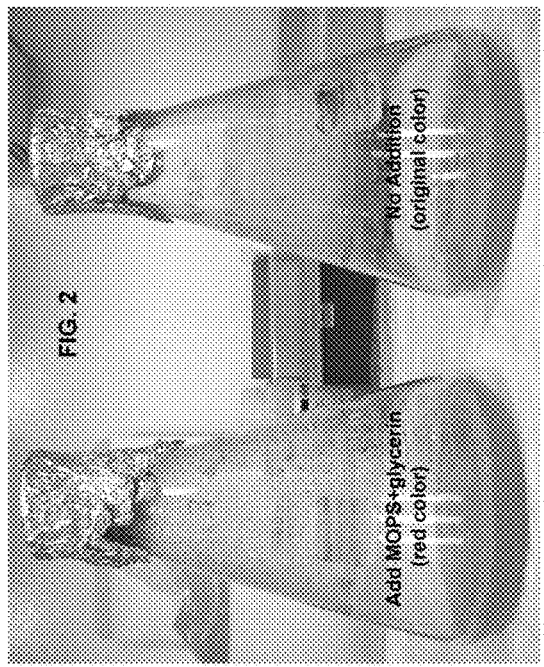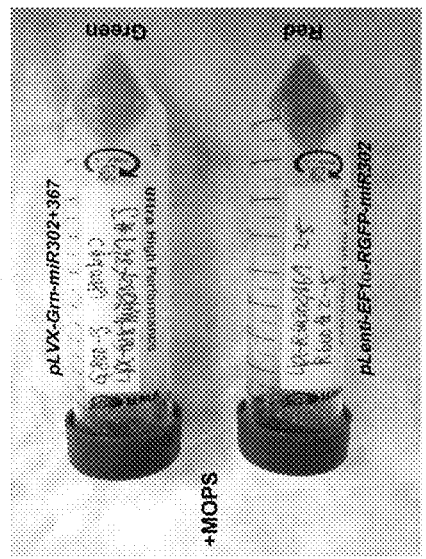

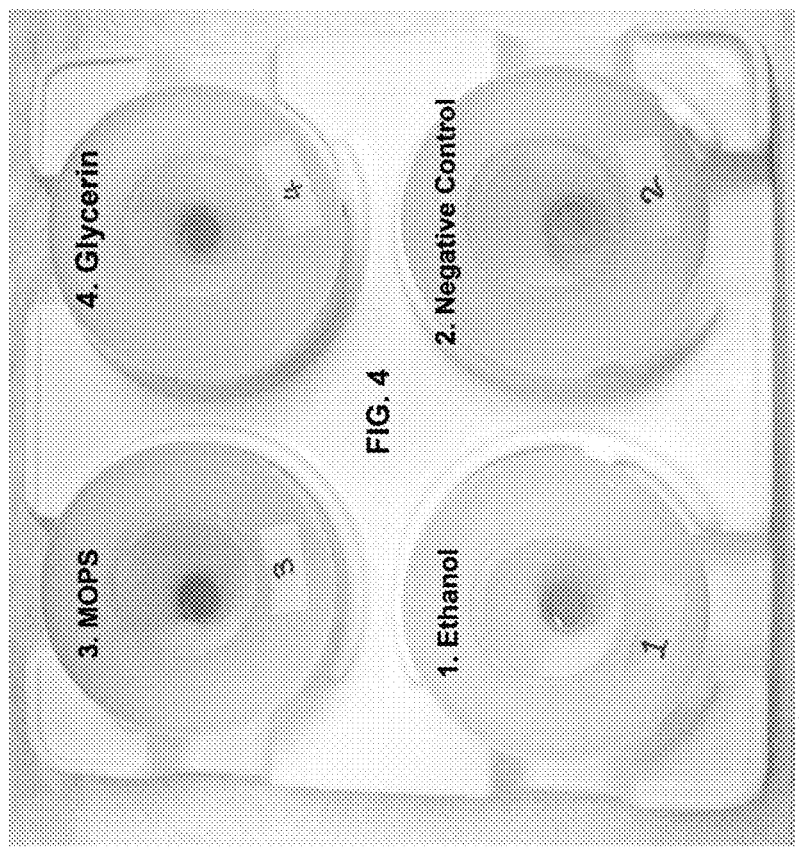

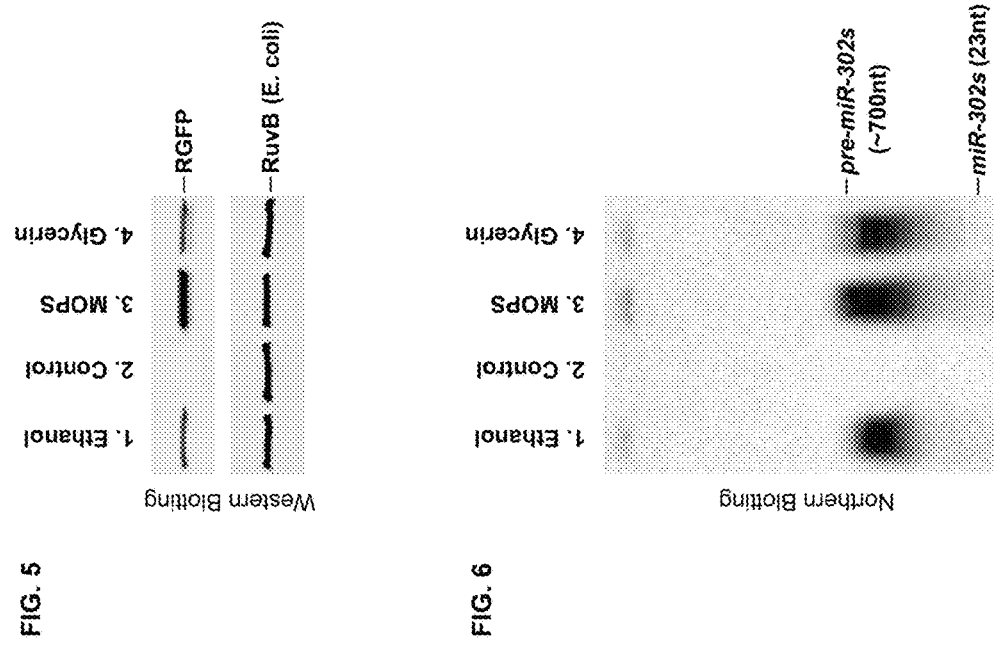

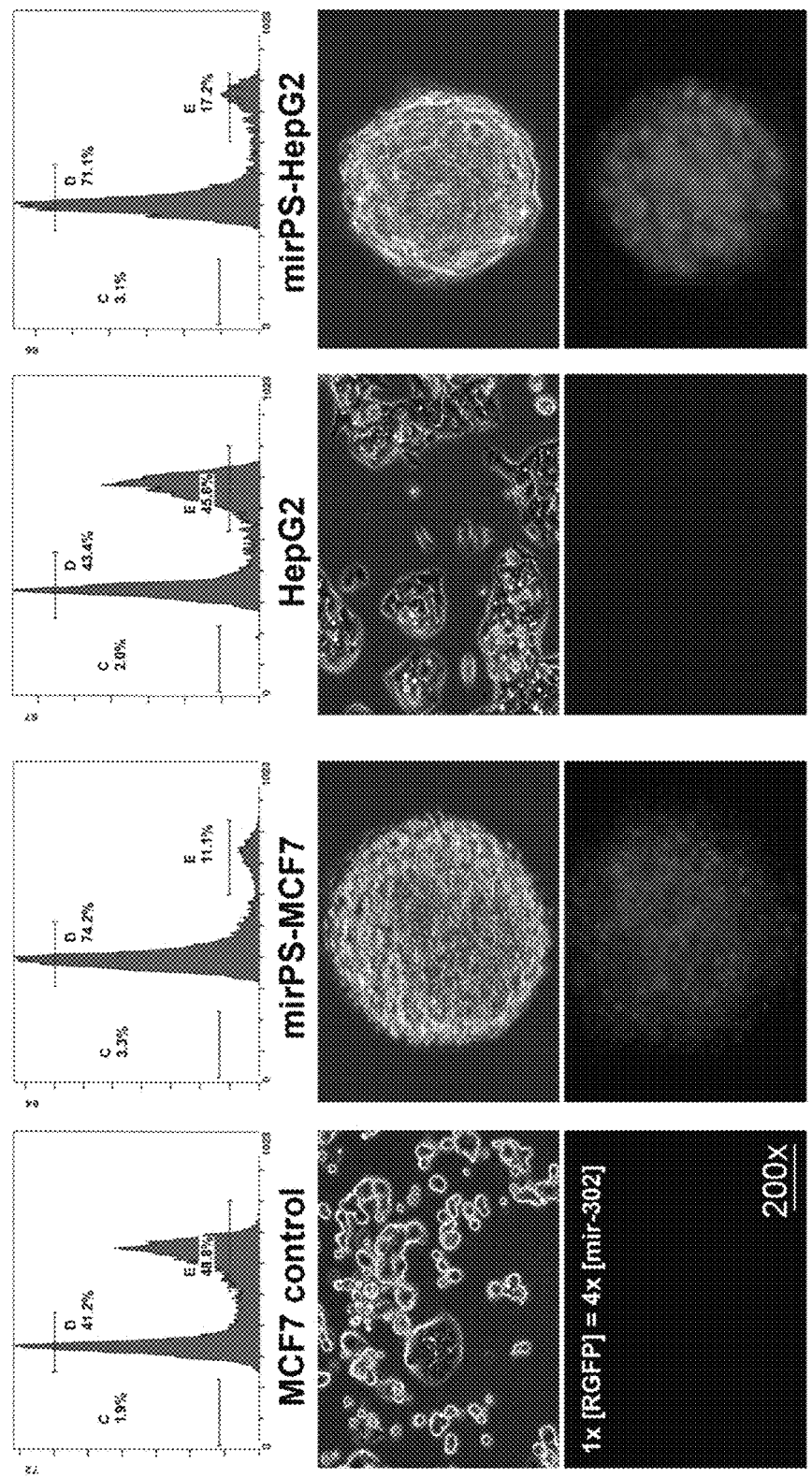

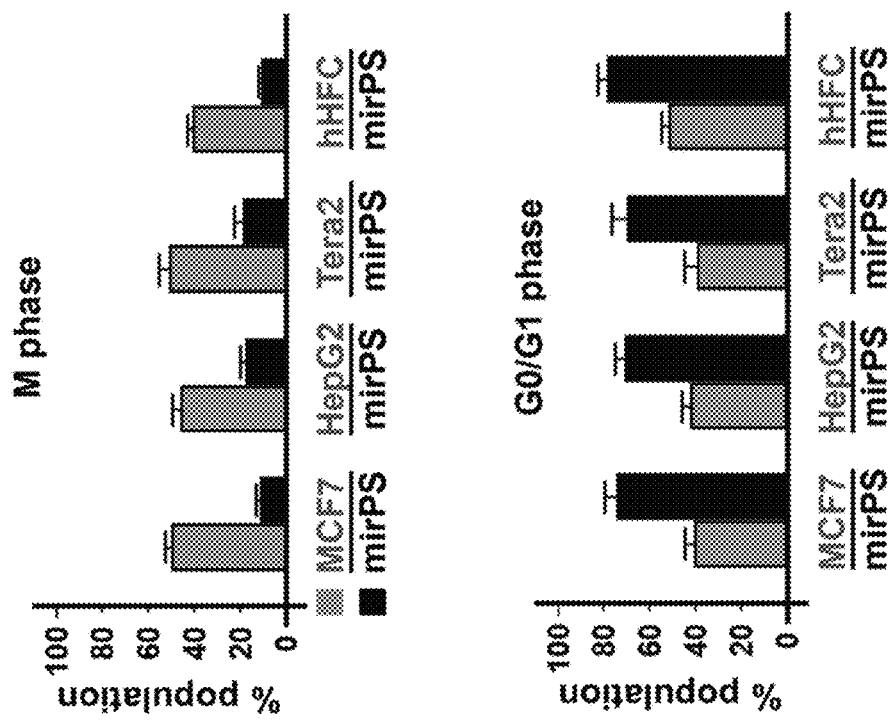
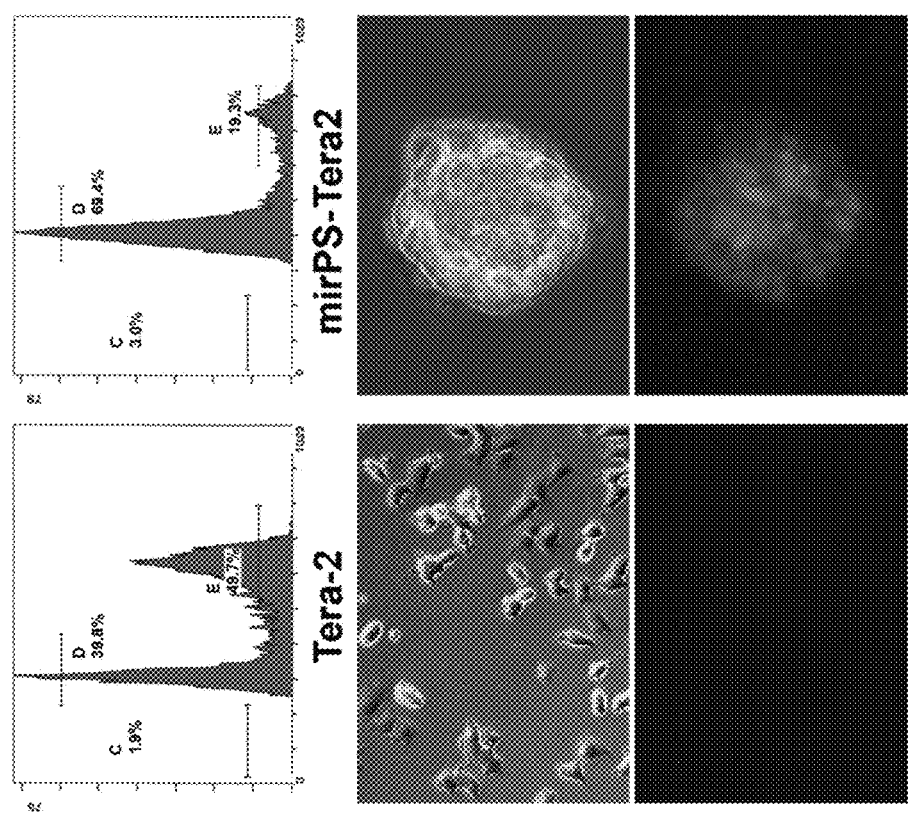

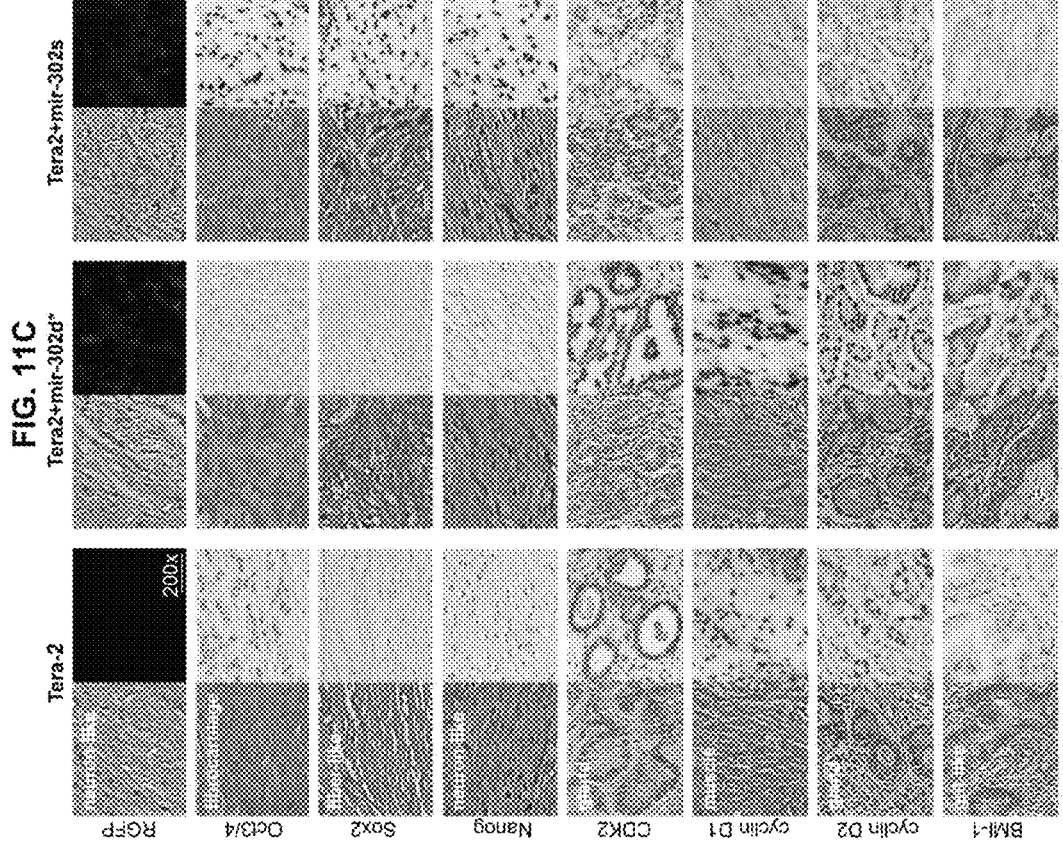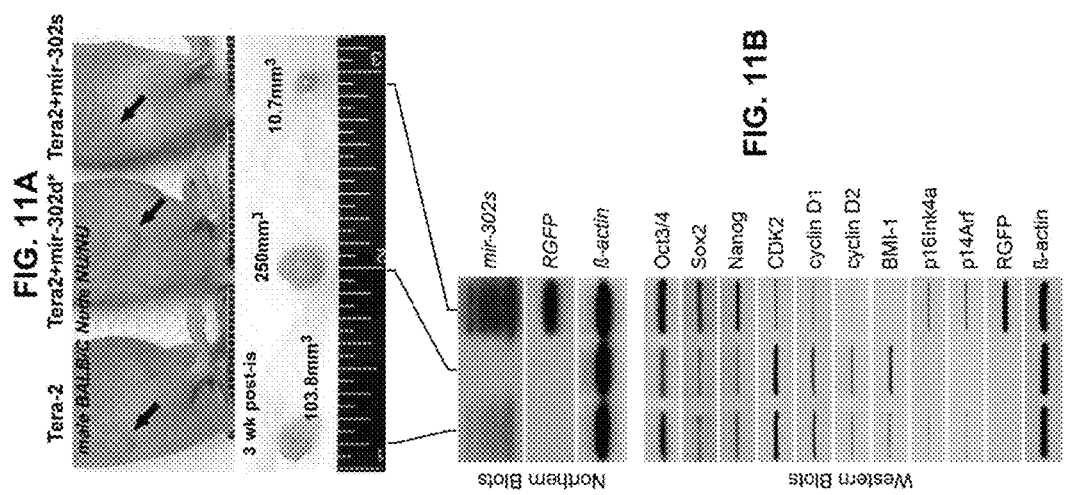

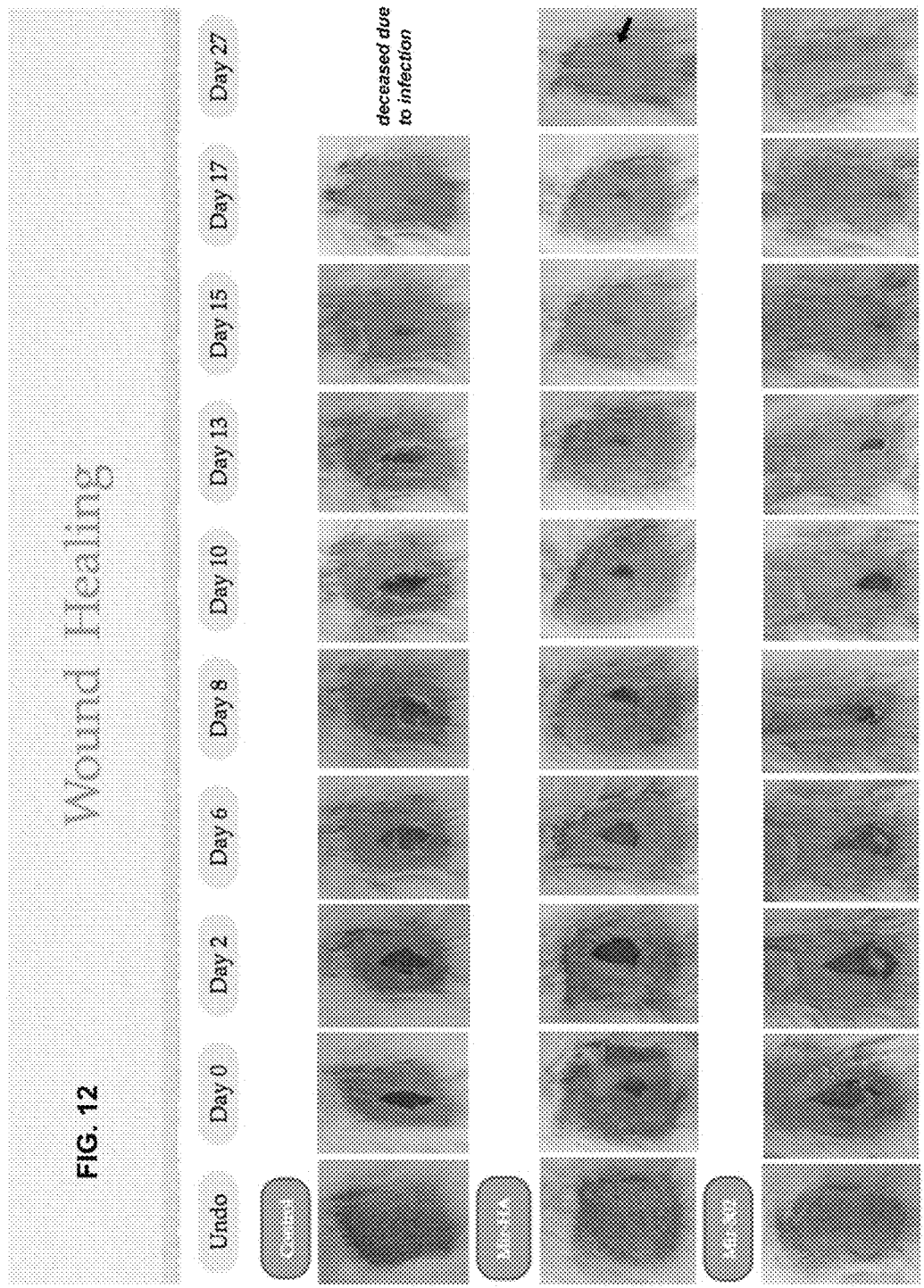

INDUCIBLE GENE EXPRESSION COMPOSITION FOR USING EUKARYOTIC POL-2 PROMOTER-DRIVEN TRANSCRIPTION IN PROKARYOTES AND THE APPLICATIONS THEREOF

CROSS REFERENCE TO RELATED APPLICATIONS

This application is a Divisional of copending application Ser. No. 13/572,263, filed on Aug. 10, 2012, which claims the benefit under 35 U.S.C. §119(e) to U.S. Provisional Application No. 61/522,843, filed on Aug. 12, 2011, all of which are hereby expressly incorporated by reference into the present application.

BACKGROUND OF THE INVENTION

Field of Invention

This invention generally relates to a composition and its application for producing ribonucleic acids (RNAs, i.e. messenger RNAs and microRNAs) and/or proteins/peptides (i.e. antibodies and enzymes) using eukaryotic RNA promoter-driven transcription in prokaryotes. Particularly, the present invention teaches a composition and its use for generating RNAs and/or proteins/peptides using eukaryotic type II RNA polymerase (pol-2) promoter-driven transcription in bacterial cells. Alternatively, the present invention is also an inducible gene expression composition using chemical agents rather than antibiotics to stimulate eukaryotic RNA promoter-driven transcription in prokaryotes. The novelty of the present invention is to induce a quick adaptation of prokaryotic cells to use eukaryotic pol-2 promoters for directly expressing desired RNAs and/or proteins/peptides without the need of changing to error-prone prokaryotic promoters or growing laborious and costly hybridomas or mammalian cells and to improve the reading fidelity of the transcription in the prokaryotes. The ribonucleic acids and proteins/peptides so obtained can be used to develop drugs, cure diseases, treat tumors/cancers, produce pluripotent stem (iPS) cells, enhance wound healing, and provide food supply.

Description of Related Art

As learning from current textbooks, any one of ordinary skill in the art has known very well that prokaryotic and eukaryotic transcription machineries contain differences and are not compatible to each other. For example, based on current understandings, eukaryotic RNA polymerases do not bind directly to promoter sequences and require additional accessory proteins to initiate transcription, whereas prokaryotic RNA polymerases form a holoenzyme that binds directly to promoter sequences to initiate transcription. It is also a common knowledge for an ordinary skill in the art to know that eukaryotic messenger RNA (mRNA) is synthesized in the nucleus by type II RNA polymerases (pol-2) and then processed and exported to the cytoplasm for protein synthesis, whereas prokaryotic RNA transcription and protein translation take place simultaneously off the same piece of DNA in the same place. Prokaryotes such as bacteria and archaea do not have a nucleus-like structure. These differences make a prokaryotic cell difficult or even impossible to produce eukaryotic RNAs and peptides/proteins using eukaryotic RNA promoters.

Prior art attempts at producing mammalian peptides and/or proteins in bacterial cells, such as U.S. Pat. No. 7,959,926 to Buechler and U.S. Pat. No. 7,968,311 to Mehta, used bacterial or bacteriophage promoters. For expression, the complementary DNA (cDNA) of a desired gene was cloned into a plasmid vector behind a bacterial or bacteriophage promoter. The cDNA of the desired gene must not contain any non-coding intron because bacteria do not have RNA splicing machineries to process the intron. Then, the vector so obtained was introduced into a competent strain of bacteria, such as *Escherichia coli* (*E. coli*), for expressing the desired gene transcripts (mRNAs) and further translating the mRNAs into proteins. Nevertheless, these bacterial and bacteriophage promoters, such as Tac, Lac, T3, T7, and SP6 RNA promoters, are not pol-2 promoters and their transcription is an error-prone process that tends to cause mutations. On the other hand, Mehta also taught that glycerol might be used to increase the efficiency of bacterial transformation; however, no description was related to enhancing promoter-driven RNA transcription, in particular pol-2 promoter-driven transcription. Due to lack of possible compatibility between eukaryotic and prokaryotic transcription systems, these prior arts were still limited by the use of prokaryotic RNA promoters in prokaryotes.

Traditional inducible gene expression methods, such as the old teaching from Gossen M. and Bujard H. (1992) and U.S. Pat. No. 5,464,758 to Gossen, required the use of antibiotics (e.g. tetracycline or doxycycline) to stimulate the activation and expression of a tetracycline-responsive-element (TRE)-controlled cytomegaloviral (CMV) or pol-3 (U6) promoter, namely Tet-On promoter. However, these Tet-On promoters are not eukaryotic pol-2 promoters and have never been tested in prokaryotes. Hence, if we can induce the adaptation of prokaryotic transcription machineries to express from eukaryotic pol-2 promoters, a novel inducible gene expression system will be made simply based on the differences between prokaryotic and eukaryotic transcription mechanisms rather than the previously toxic induction methods of using antibiotics, which may inhibit the growth of prokaryotes.

SUMMARY

The present invention provides a novel breakthrough to the old textbook concept regarding incompatibility between prokaryotic and eukaryotic transcription systems. By adding some chemical agents, we now can induce a quick adaptation of prokaryotes for using eukaryotic pol-2 promoters to produce desired RNAs and the related peptide/protein thereof.

An object of the present invention is to provide an inducible gene expression composition for using eukaryotic pol-2 promoter-driven transcription in prokaryotes and the applications thereof.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve these and/or other objects, as embodied and broadly described, the present invention provides a composition useful for regulating eukaryotic promoter-driven gene expression in prokaryotes, comprising a chemical agent, containing a structure similar to 3-morpholinopropane-1-sulfonic acid (MOPS), ethanol, glycerin, or a mixture thereof.

In another aspect, the present invention provides a composition for regulating eukaryotic promoter-driven gene expression in prokaryotes, comprising: (a) at least a chemical agent capable of inducing or enhancing eukaryotic promoter-driven gene expression, wherein said chemical agent containing a structure similar to 3-morpholinopropane-1-sulfonic acid (MOPS), ethanol, glycerin, or a mixture thereof; and (b) a plurality of prokaryotic cells, said plurality of prokaryotic cells containing at least a gene mediated by a eukaryotic promoter-driven expression mechanism; wherein (a) and (b) are mixed together under a condition to induce the eukaryotic promoter-driven gene expression of said gene in said prokaryotic cells.

It is to be understood that both the foregoing general description and the following detailed description are exemplary and explanatory and are intended to provide further explanation of the invention as claimed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 depicts the results of bacterial culture broths treated with (left) or without (right) the mixture of 0.1% (v/v) MOPS and 0.05% (v/v) glycerin.

FIG. 3 shows the results of different bacterial pellets after treated with 0.1% (v/v) MOPS.

FIG. 4 shows the inducibility of different chemicals for inducing pol-2 promoter-driven gene expression in competent E. coli DH5alpha cells.

FIG. 5 shows the Western blotting results of red RGFP protein expression induced by MOPS, glycerin and ethanol, respectively.

FIG. 6 shows the Northern blotting results of miR-302 and its pre-miRNA cluster expression induced by MOPS, glycerin and ethanol, respectively.

FIGS. 9A-9C and 10A-10B show in vitro tumorigenicity assays of various tumor/cancer cells in response to miR-302 and/or pre-miR-302 treatment.

FIGS. 11A-11C show in vivo tumorigenicity assays of embryonal teratocarcinoma Tera-2 cells in response to either the whole miR-302 familial cluster (Tera2+mir-302s) or antisense miR-302d only (Tera2+mir-302d*) treatment (n=3, p<0.05).

FIG. 12 shows the results of an in-vivo wound healing trial using microRNA miR-302 and/or pre-miR-302 containing ointment to treat skin open wounds in mice.

DETAILED DESCRIPTION

Figure 1A:
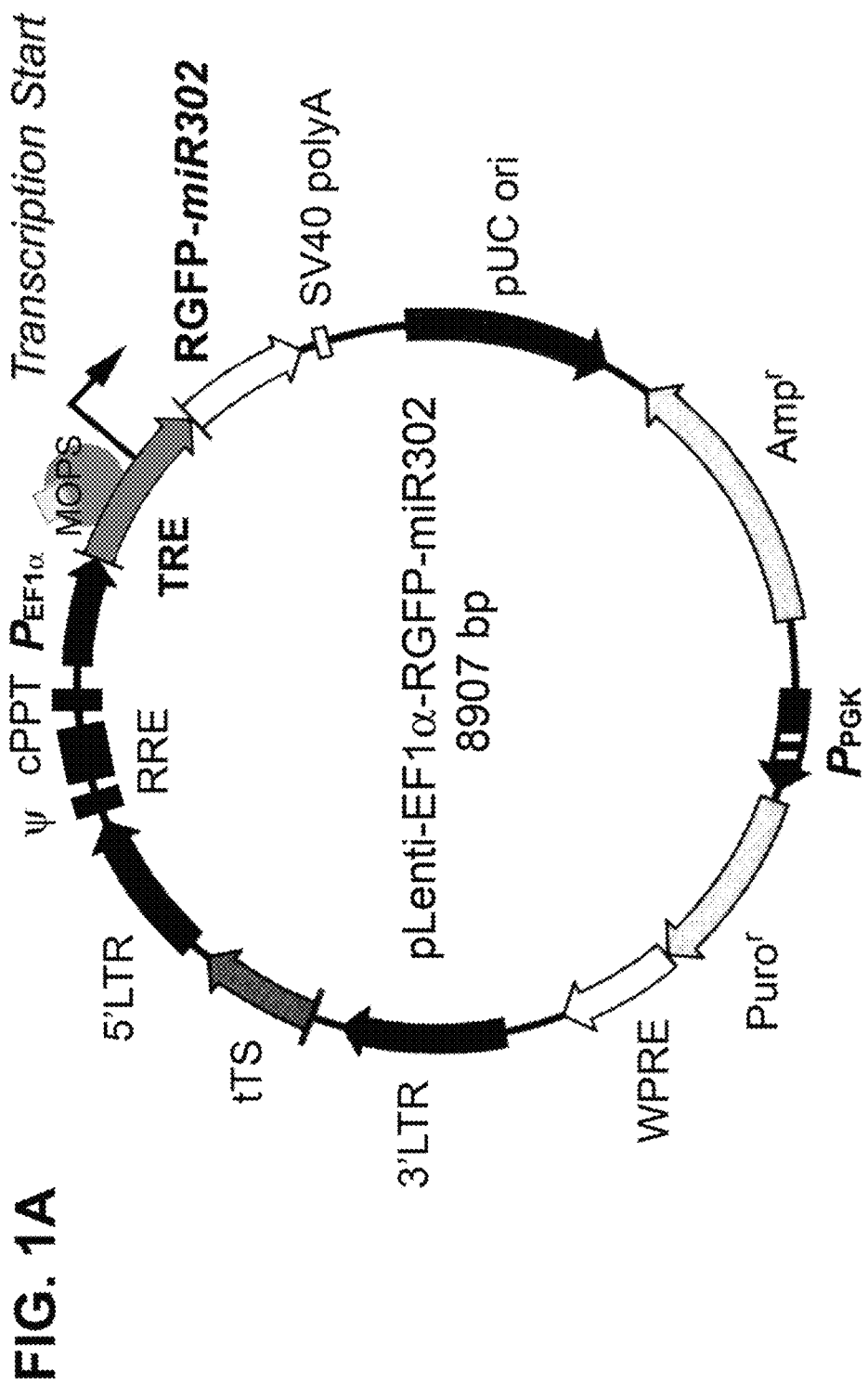
FIGS. 1A and 1B show an inducible pol-2 promoter-driven gene expression composition (A) and its mechanisms (B) for RNA transcript and protein production in prokaryotes and eukaryotes and microRNA (miRNA) production in eukaryotes.

The principle of the present invention is relied on the different and incompatible properties between prokaryotic and eukaryotic gene transcription systems. Normally, prokaryotic RNA polymerases do not recognize eukaryotic promoters and vise versa. However, the present invention has identified a plurality of chemical agents that can serve as transcription inducers to induce and/or enhance the eukaryotic promoter-driven gene expression in prokaryotes. The same or other chemical agents may also serve as transcription inducers to induce and/or enhance the prokaryotic promoter-driven gene expression in eukaryotes. Hence, the novelty and knowledge taught in the present invention has provided a complete breakthrough to current understanding in the differences between prokaryotic and eukaryotic transcription mechanisms.

The transcription inducers found in the present invention are normally not preferred to be used in a cell culture condition. In all chemicals tested, the top three most potent inducers are 3-morpholinopropane-1-sulfonic acid (or named 3-(N-morpholino)propanesulfonic acid; MOPS), glycerin and ethanol. Their induction capability is found to be dose-dependent in proportional to their concentrations. Some chemicals containing a structure similar to MOPS, ethanol and/or glycerin may also have the same functionality. MOPS is frequently used as a buffering agent in bacterial lysis and plasmid extraction and hence is not recommended for bacterial cell culture. Ethanol is known to be a bacterial sanitizer. Glycerin can be used to increase transformation efficiency by destabilizing bacterial cell walls, yet is not recommended for bacterial cell culture. Both glycerin and ethanol are also viable preserving agents in that glycerin is bacteriostatic and ethanol is bactericidal in its action, respectively. In view of all these known functionalities to MOPS, ethanol and glycerin, an ordinary skill in the art would not anticipate the use of a trace amount (0.01% to 1% volume/volume concentration) of these chemicals for inducing eukaryotic promoter-driven gene expression in prokaryotic cells without first knowing the knowledge of the present invention.

The present invention is an inducible gene expression composition using certain chemical agents to stimulate and/or increase eukaryotic promoter-driven RNA transcription and the related peptide/protein synthesis in prokaryotes. An inducible gene expression composition comprises (a) at least a chemical agent containing a structure similar to MOPS, ethanol or glycerin, or a mixture thereof; and (b) a plurality of prokaryotic cells that contain at least a gene mediated by a eukaryotic pol-2 promoter-driven or a pol-2 compatible viral promoter-driven expression mechanism; wherein (a) and (b) are mixed together under a condition to induce the expression of said gene. The present invention also provides a novel composition design and its application for inducing a quick adaptation of prokaryotes to use eukaryotic pol-2 promoters for directly expressing RNAs and/or proteins/peptides of interest without the need of changing to error-prone prokaryotic promoters or growing laborious and costly hybridomas or mammalian cells and for improving the reading fidelity of prokaryotic transcription, i.e. providing a pol2-like transcription mechanism. The RNAs expressed are preferably eukaryotic RNAs (i.e. messenger RNAs and microRNAs), and the proteins/peptides includes antibodies and enzymes.

Preferably, said prokaryote is a bacterial cells in particular, Escherichia coli (E. coli), and said chemical agent is 3-morpholinopropane-1-sulfonic acid (MOPS), ethanol or glycerin, or a mixture thereof. Also preferably, said eukaryotic RNA promoter is either a eukaryotic pol-2 promoter (i.e. EF1alpha) or a pol-2 compatible viral promoter (i.e. cytomegaloviral promoter or retroviral long terminal repeat promoter). The gene mediated by said eukaryotic RNA promoter is coded for either a non-coding or a protein-coding RNA transcript, or both, selected from the group consisted of microRNA (miRNA), small hairpin RNA (shRNA), small interfering RNA (siRNA), messenger RNA (mRNA), their precursors and homologs, and a combination thereof. The peptide/protein generated by the present invention is translated from the above protein-coding mRNA transcripts and may be selected from, but not limited to, the group consisted of enzyme, growth factor, antibody, insulin, botulinum toxin (botox), any functional protein and it homologs, and a combination thereof. Preferably, said condition for inducing the expression of said gene is a bacterial culturing condition in Luria-Bertani (LB) broth at 37° C. with the addition of said chemical agents.

Figure 1B:
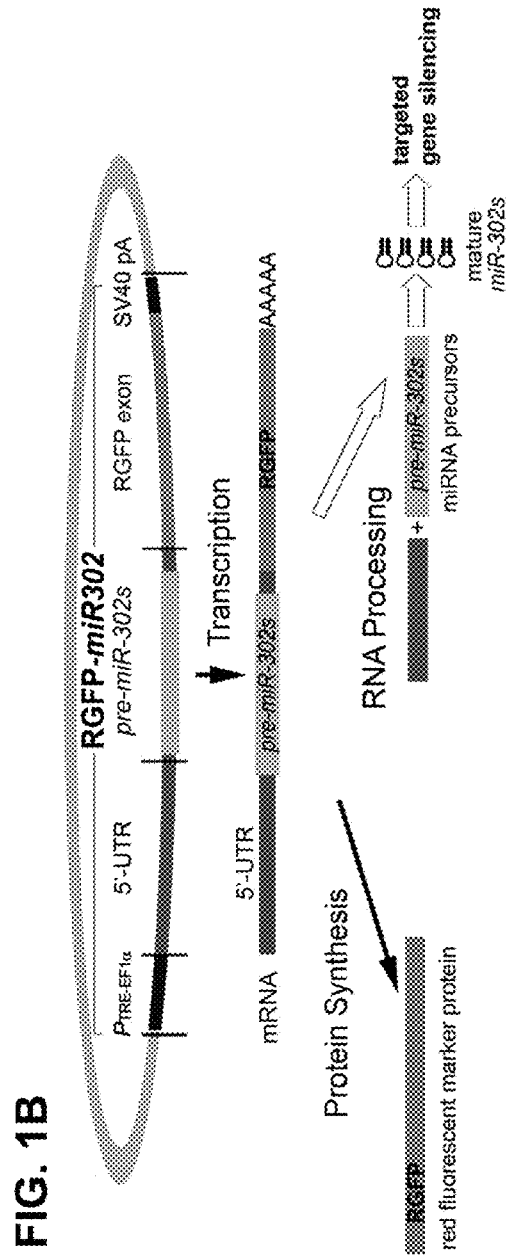

To demonstrate the inducibility of said chemical inducers for RNA and protein production in prokaryotes, the present invention adopted and modified a lentiviral plasmid vector, e.g. pSpRNAi-RGFP-miR302, from the U.S. patent application Ser. No. 12/149,725 and Ser. No. 12/318,806 to Lin, and then used the red fluorescent protein (RGFP) gene cloned into the vector as a visible marker for measuring the process of RNA transcription and protein synthesis, as shown in FIG. 1B. The original cytomegaloviral (CMV) promoter of the pSpRNAi-RGFP-miR302 vector has been replaced by human pol-2 EF1alpha promoter in this invention and herein formed a new plasmid vector, named pLenti-EF1alpha-RGFP-miR302, as shown in FIG. 1A. Additionally, since prokaryotes can not process any in-frame intron, the SpRNAi intron of the RGFP gene has been removed and the original intron-encoded miR-302 cluster was moved to the 5'-untranslated region (5'-UTR) of the RGFP gene, so as to form a RGFP-miR302 gene. Broadly speaking, the 5'-UTR and 3'-UTR of a gene can be considered as an extension of intron. Thus, miR-302 expression disclosed here is still based on the same intronic microRNA biogenesis mechanism described in the scope of prior U.S. patent application Ser. No. 12/149,725 and Ser. No. 12/318,806. Advantageously, due to lack of RNA splicing in prokaryotes, the miR-302 transcripts so obtained in the present invention remain as hairpin-like microRNA precursors (pre-miRNA or pri-miRNA), which can be further purified and delivered into eukaryotic cells for forming mature miR-302 and eliciting the function of miR-302 (FIG. 1B).

Induction of Eukaryotic Promoter-Driven Protein-Coding Gene Expression in Prokaryotes

*Escherichia coli* (*E. coli*) is transformed by the pLenti-EF1alpha-RGFP-miR302 plasmid vector using, a z-competent *E. coli* transformation kit (Zymo Research, Irvine, Calif.) and cultivated in Luria-Bertani (LB) broth at 37° C. with frequent agitation at 170 rpm. After overnight incubation, the *E. coli* culture supplemented with a mixture of 0.1% (v/v) MOPS and 0.05% (v/v) glycerin expresses highly abundant red RGFP proteins that clearly stain the bacterial LB broth in red, whereas the blank control culture fails to produce any RGFP, as shown in FIG. 2. The presence of functional RGFP indicates that both its RNA and protein are successfully produced.

To further confirm the specificity of protein induction by the identified chemicals like MOPS, two transformed *E. coli* strains are prepared: one carries a pLVX-Grn-miR302+367 plasmid vector having a CMV promoter-driven green fluorescent protein (GFP) gene and the other carries the aforementioned pLenti-EF1alpha-RGFP-miR302 vector. After overnight incubation with 0.1% (v/v) MOPS, the *E. coli* transformed with pLVX-Grn-miR302+367 produces green cells while the other with pLenti-EF1alpha-RGFP-miR302 shows red cells, as shown in FIG. 3. This result indicates that chemicals like MOPS can induce specific RNA and it related protein production either from a eukaryotic pol-2 promoter or a pol-2 compatible viral promoter. Also, the induced RNA and protein production is highly specific and can be regulated by the chemical added. It is particularly noted that the protein production is so abundant that even the bacterial cells are visually stained by respective colors.

Among all chemicals tested in the present invention, the top three most potent inducers are MOPS, glycerin and ethanol, as shown in FIG. 4. The quantitative result of the induced RGFP protein production is further confirmed by Western blot analysis, as shown in FIG. 5 and Example 3. Bacterial RuvB protein is served as a house-keeping standard to normalize the RGFP expression. The inducibility of these identified inducers is also found to be dose-dependent in proportional to their concentrations. Without any treatment, negative control *E. coli* cells just show their original bacterial color in absence of any fluorescent stain. Therefore, according to all these results, the present invention clearly provides a novel chemical-inducible composition and its application for modulating eukaryotic pol-2 promoter-driven or pol-2 compatible viral promoter-driven gene expression in prokaryotic cells. The gene product can be either RNA or protein/peptide, or both. In view of the above demonstration, it is very obvious for an ordinary skill in the art to use other intron-free genes or the related cDNAs in place of the RGFP gene for producing functional RNAs and/or proteins in prokaryotes.

Induction of Eukaryotic Promoter-Driven Non-Coding RNA Expression in Prokaryotes As mentioned above that the pLenti-EF1alpha-RGFP-miR302 vector contains a microRNA miR-302 cluster in the 5'-UTR of the RGFP gene (FIGS. 1A and 1B), the induced expression of the RGFP gene will also generate the miR-302 cluster (pre-miR-302s) as shown in the schematic mechanism of FIG. 1B. Due to lack of RNA splicing machinery (e.g. spliceosome) in prokaryotes, miR-302 cluster so obtained in the present invention are found to remain as hairpin-like microRNA precursors (pre-miR-302s or pri-miR-302s), which are very useful for being isolated and delivered into eukaryotic cells. In eukaryotic cells, these pre-miR-302s or pri-miR-302s can be further processed into mature miR-302s (i.e. the miR-302 microRNAs) for eliciting the miR-302 function. Similarly, other kinds of microRNAs and the related precursors thereof can be produced following the same protocol for miR-302 expression. Alternatively, some non-coding RNAs such as short interfering RNAs (siRNAs) and small hairpin RNAs (shRNAs) can be designed to mimic the above microRNA expression. These non-coding RNAs preferably contain at least a sequence sharing 30% to 100% homology to a microRNA. Also, these shRNAs/siRNAs may contain perfectly matched hairpin stem regions, while mammalian microRNA precursors (pre-miRNAs or pri-miRNAs) often contain mismatched base pairs. Given that most of microRNAs function as specific gene silencers and may play a variety of distinctive roles in many physiological and pathological mechanisms, including but not limited to biological development, stem cell generation, nuclear reprogramming, cell differentiation, cell cycle regulation, tumor suppression, immunological defense, apoptosis, rejuvenation, wound healing, and many more, the potential applications in theses pharmaceutical and therapeutical fields are highly expected. Both of the transduced plasmid vector and the non-coding RNA (i.e. microRNA/shRNA) can be simultaneously amplified in the prokaryotic cells, such as *E. coli*. The method for isolating the amplified pLenti-EF1alpha-RGFP-miR302 plasmid DNA and the transcribed pre-miR-302s/pri-miR-302s is disclosed in Examples 5 and 6. The method for delivering the amplified non-coding RNA (i.e. pre-miR-302s/pri-miR-302s) and/or the vector (i.e. pLenti-EF1alpha-RGFP-miR302) into eukaryotes may be selected from the group of endocytosis, glycerol infusion, peptide/liposomal/chemical-mediated transfection, electroporation, gene gun penetration, microinjection, transposon/retrotransposon insertion, and adenoviral/retroviral/lentiviral infection.

Corresponding to the RGFP induction experiments shown above (FIGS. 4 and 5), we also measure the expression of non-coding pre-miR-302s and its mature miR-302 products in the pLenti-EF1alpha-RGFP-miR302-transformed bacteria with or without chemical induction. As shown in FIG. 6 and Example 4, the quantitative result of induced pre-miR-302s production has been confirmed by Northern blot analysis. Similar to the results of the RGFP induction experiments (FIGS. 4 and 5), the pre-miR-302s expression is detected in transformed bacteria treated with MOPS, glycerin or ethanol, but not blank control, indicating that these chemical pol-2 promoter inducers are also able to trigger non-coding RNA expression in prokaryotic cells as well. Due to the structural similarity of all microRNAs (miRNAs) and shRNAs, it is obvious for an ordinary skill in the art to use other non-coding miRNAs and/or shRNAs in place of the miR-302 cluster for producing functional miRNAs, shRNAs and/or their precursors/homologs in prokaryotes.

Functional Application of the Present Invention in Stem Cell Generation

MicroRNA miR-302 has been used to reprogram mammalian somatic cells to embryonic stem cell (ESC)-like induced pluripotent stem (iPS) cells as demonstrated in the U.S. patent application Ser. No. 12/149,725 and Ser. No. 12/318,806. Many stem cell applications and therapies have been developed dependent on these ESC-like iPS cells. However, miR-302 is only produced abundantly in human ESCs rather than other differentiated tissue cells. Isolation of human ESCs is highly debatable. Cultivation of human ESCs is also very laborious and costly. Making synthetic miR-302 mimics is an alternative way to bypass the need of human ESCs, yet still very expensive and inefficient. The similarity between synthetic and natural miR-302 is also questionable. To solve these problems, the present invention can provide a simple, cheap, fast and inducible composition and method for the bulk production of miR-302 and/or its precursors/homologs in prokaryotes. Moreover, the isolation of miR-302 and/or its precursors from prokaryotic cells is relatively easy and cost-effective, as shown in FIG. 6 and Example 6 of the present invention.

Figure 7:
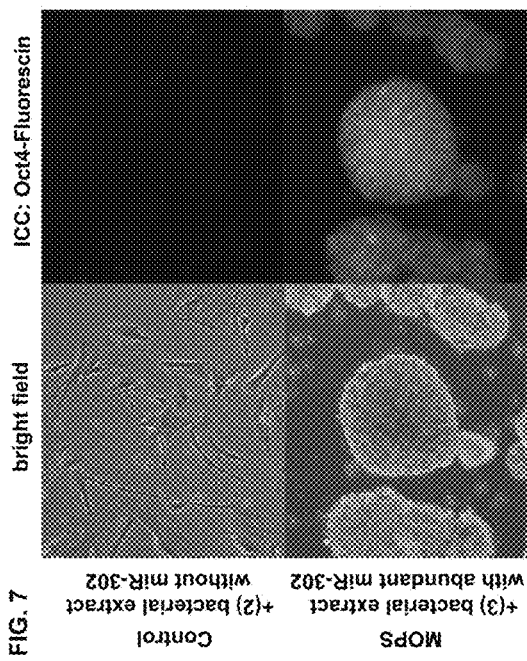
FIG. 7 shows iPS cell generation using miR-302 and/or pre-miR-302 isolated from bacterial extracts (BE), which is confirmed by Northern blot analysis as shown in FIG. 6.

We have used the pLenti-EF1alpha-RGFP-miR302-transformed *E. coli* cells to produce and isolate high quantity and quality of pLenti-EF1alpha-RGFP-miR302 vector and pre-miR-302s, as shown in Examples 5 and 6. Both pLenti-EF1alpha-RGFP-miR302 and pre-miR-302s are expected to be useful for generating iPS cells in view of the U.S. patent application Ser. No. 12/149,725 and Ser. No. 12/318,806. Following Example 2, when the pre-miR-302s produced by the present invention are transduced into human skin primary keratinocytes, the transfected keratinocytes are reprogrammed to ESC-like iPS cells and express strong ESC marker Oct4 (FIG. 7). Further shown in FIG. 8 and Example 8, bisulfite DNA sequencing assay also shows that global DNA demethylation occurs in the promoter regions of Oct4 and Sox2 genes, two of the most important reprogramming factors and ESC markers. As global DNA demethylation and Oct4 expression are known to be the first step that cells have successfully begun the process of reprogramming to attain ESC-like pluripotency (Simonsson and Gurdon, *Nat Cell Biol.* 6: 984-990, 2004), the miR-302 and/or pre-miR-302 isolated from the MOPS-induced bacterial extracts is proven to be effective for iPS cell generation. This example confirms that the present invention can be used to prepare abundant miR-302 and/or pre-miR-302-containing bacterial extracts or lysates for pluripotent stem cell generation.

Application of microRNA Extracts in Tumor/Cancer Therapy

We may produce abundant microRNA miR-302 precursors (pre-miR-302s or pri-miR-302s) and the related miR-302-encoding plasmid vectors using the present invention (Examples 1, 5 and 6). The function and mechanism of using miR-302 in cancer therapy can be referred to the U.S. patent application Ser. No. 12/318,806 and Ser. No. 12/792,413. Our previous studies have also demonstrated the feasibility of this approach in treating human melanoma, prostate cancer (Lin et al., RNA 2008), breast cancer, hepatocellular carcinoma, and embryonal teratocarcinoma cells (Lin et al., *Cancer Res.* 2010). As shown in FIGS. 9A-9B, all tested tumor/cancer cells were reprogrammed to normal iPS cells and formed embryoid body-like cell colonies after miR-302 and/or pre-miR-302 treatment. The cells obtained after miR-302 and/or pre-miR-302 treatment are labeled as mirPS cells, abbreviated for "miR302-induced pluripotent stem cells". Moreover, miR-302 was also found to induce significant apoptosis (>95%) in all tested tumor/cancer cells but not normal tissue cells (Lin et al., *RNA* 2008 and *Cancer Res.* 2010). Flow cytometry analysis comparing DNA content to cell cycle stages, further showed a significant reduction in all mirPS mitotic cell populations (FIG. 9C). The mitotic cell population (M phase) was decreased by 78% from 49%±3% to 11%±2% in mirPS-MCF7, by 63% from 46%±4% to 17%±2% in mirPS-HepG2, and by 62% from 50%±6% to 19%±4% in mirPS-Tera2 cells, whereas the resting/dormant cell population (G0/G1 phase) was increased by 80% from 41%±4% to 74%±5% in mirPS-MCF7, by 65% from 43%±3% to 71%±4% in mirPS-HepG2, and by 72% from 40%±7% to 69%±8% in mirPS-Tera2 cells, respectively. These results indicate that miR-302 and/or pre-miR-302 can effectively attenuate the fast cell cycle rates and cause significant apoptosis in these tumor/cancer cells.

Figure 10A:
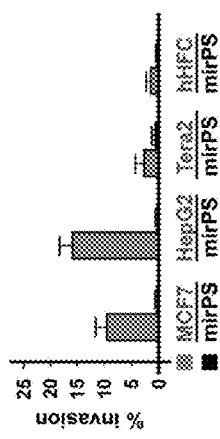
Figure 10B:
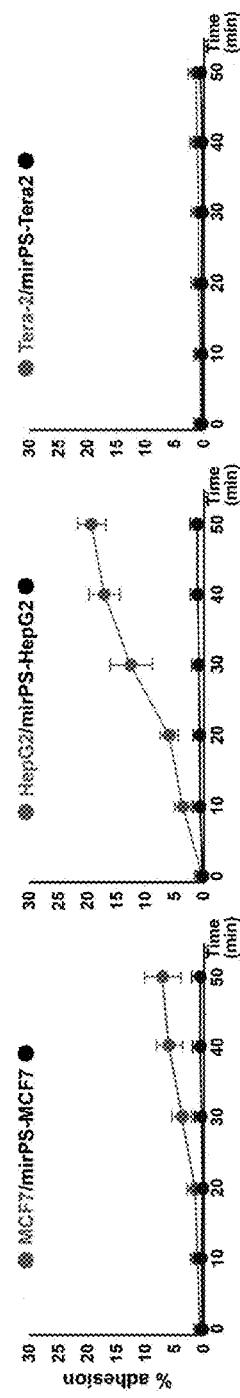

In vitro tumorigenicity assays, using Matrigel chambers (cell invasion assay, Example 9) and cell adhesion to the human bone marrow endothelial cell (hBMEC) monolayer (cell adhesion assay, Example 10), revealed two more anti-tumorigenetic effects of miR-302 and/or pre-miR-302 in addition to its anti-proliferative feature. Cell invasion assay showed that all mirPS-tumor/cancer cells lost their ability to migrate (reduced to <1%) while the original tumor/cancer cells aggressively invaded into the chambered areas supplemented with higher nutrients, representing over 9%±3% of MCF7, 16%±4% of Hep G2 and 3%±2% of Tera-2 cell populations (FIG. 10A). Consistently, cell adhesion assay also showed that none of these mirPS-tumor/cancer cells could adhere to hBMECs whereas a significant population of original MCF7 (7%±3%) and Hep G2 (20%±2%) cells quickly metastasize into the hBMEC monolayer after 50 min incubation (FIG. 10B). In sum, all of the findings thus far strongly and repeatedly suggest that miR-302 and/or pre-miR-302 is a human tumor suppressor capable of attenuating fast cell growth, causing tumor/cancer cell apoptosis, and inhibiting tumor/cancer cell invasion as well as metastasis. Most importantly, this novel miR-302 and/or pre-miR-302 function may offer a universal treatment against multiple kinds of human cancers/tumors, including but not limited in malignant skin, prostate, breast, and liver cancers as well as various tumors in view of the variety of different tissue types in embryonal teratomas.

After identifying the tumor suppressor function of miR-302 and/or pre-miR-302 and its different effects on normal and tumor/cancer cells, we have further tested the possible use of miR-302 and/or pre-miR-302 as an anti-cancer drug for treating Tera2-derived teratomas in eight-week-old male athymic mice (BALB/c nu/nu strain) (FIGS. 11A-11C and Examples 11 and 12). Tera-2 cells are originally derived from human embryonal teratocarcinomas that contain a variety of primitive tumorous tissue cells. Due to this pluripotent feature, Tera2-derived teratomas often serve as a treatment model for various tumor types in vivo. As shown in FIG. 11A, after miR-302 and/or pre-miR-302 treatment (Tera2+mir-302s) for three weeks, we detected a significant reduction of the average tumor size by >89% (11±5 mm$^3$, n=6) compared to that of non-treated ones (104±23 mm$^3$, n=4). In contrast, treating the same amount of antisense-mir-302d (Terat2+mir-302d*) increased the average tumor sizes by 140% (250±73 mm$^3$, n=3). Northern blotting also showed that miR-302 expression levels in these differently treated teratoma cells negatively correlated to the tumor sizes (FIG. 11B), suggesting that modulating miR-302 expression can effectively control the tumor growth in vivo. To validate these findings, we further performed western blotting to confirm the co-suppression of G1-checkpoint regulators CDK2, cyclins-D1/D2 and BMI-1 and the co-activation of tumor suppressors p16Ink4a and p14/p19Arf as well as core reprogramming factors Oct3/4, Sox2 and Nanog in the miR-302 and/or pre-miR-302-treated teratomas (FIG. 11B). The same results were also confirmed by immunohistochemical (IHC) staining of these proteins in teratoma tissue sections (FIG. 11C). Based on this novel tumor suppression function of miR-302 and the consistent data in vitro and in vivo, it is conceivable that miR-302 can serve as an example microRNA for using the present invention in preparation of drugs for cancer therapy.

Application of microRNA Extracts for Wound Healing Treatment

We have tested the production of abundant microRNA miR-302 precursors (pre-miR-302s) and the related miR302-encoding plasmid vectors for use in a wound healing animal trial, using the present invention (Example 13). The pre-miR-302s and their related plasmid vectors were amplified as described in Examples 1 and 5 and extracted as described in Examples 5 and 6. Then, the isolated pre-miR-302s and their related plasmid vectors were mixed with a pre-prepared ointment base containing cocoa butter, cottonseed oil, olive oil, sodium pyruvate, and white petrolatum. The concentration of miR-302 precursors and vectors in the prepared ointment base is 10 μg/mL. Skin open wounds were generated by scalpel dissection. Ointment with or without miR-302 and/or pre-miR-302 was directly applied on the wound, respectively, and covered the whole wounded area. Then, the treated area was further sealed by liquid bandage. As show in FIG. 12, within two weeks, the results clearly showed that miR-302 and/or pre-miR-302 treatments significantly enhanced the speed of wound healing over twice faster than all other treatments and controls. Moreover, miR-302 and/or pre-miR-302-treated wound healing area showed normal hair regrowth and left no scar, while other treatments resulted in minor scar tissues with no hair (as indicated by black arrow).

Other Applications of the Present Invention

One preferred application embodiment of the present invention is to generate microRNAs and/or shRNAs for biomedical research, pharmaceutical and therapeutic applications, such as gene modulation and gene therapy. For example, but not limited, miR-302 has been found to be a tumor suppressor in human cells, as demonstrated in the U.S. patent application Ser. No. 12/318,806. The present invention may be used to produce abundant miR-302 and/or its precursors/homologs for cancer therapy or drug development. Particularly, a therapeutic microRNA/shRNA gene isolated from a microbe, plant or animal can be cloned into a plasmid vector under the control of a eukaryotic pol-2 or pol-2 compatible viral promoter and delivered into non-pathogenic bacteria. When the bacteria containing such a microRNA/shRNA expression vector is introduced into patient's cells, the patient can drink glycerin or ethanol to trigger the generation and release of the therapeutic microRNA/shRNA from the bacteria into the cells, so as to cure the disorders and/or diseases.

Another preferred application embodiment of the present invention is to generate functional proteins/peptides for biomedical research, pharmaceutical and therapeutic applications. For example, but not limited, the protein/peptide so obtained can be insulin for treating Diabetes, tumor suppressor proteins for curing tumors/cancers, growth factors for stimulating normal body development, antibodies for biomedical research or vaccine/serum production, and all varieties of biological enzymes for molecular biology and biomedical research. Particularly, a therapeutic protein/peptide gene isolated from a microbe, plant or animal can be cloned into a plasmid vector under the control of a eukaryotic pol-2 or pol-2 compatible viral promoter and delivered into non-pathogenic bacteria. When the bacteria containing such a gene vector is introduced into patient's cells, the patient can drink glycerin or ethanol to trigger the expression and release of the therapeutic protein/peptide from the bacteria into the cells, so as to cure the disorders and/or diseases.

Another one preferred application embodiment of the present invention is to generate high-yield protein food and drug supplies for humans and/or animals. Protein production by fast growing bacteria can reduce the time and labor for maintaining expensive animal stocks. Also, we can prevent unnecessary animal sacrifices. Advantageously, the present invention can even produce mammalian proteins using mammalian gene promoters, reducing the risks of genetic engineering and gene modification.

Another one possible but not preferred application embodiment of the present invention is to make biological weapons. For example, a poison/toxic protein gene isolated from a microbe, plant or animal, including but not limited to, *Bacillus anthracis*, poison ivy, jellyfish, insect, fish, amphibian, and snake, can be cloned into a plasmid vector under the control of a eukaryotic pol-2 or pol-2 compatible viral promoter and delivered into non-pathogenic bacteria. When there is no chemical agent that can induce pol-2 promoter-driven gene expression, these bacteria carrying such a plasmid vector will be stealthily amplified and present no harm to anyone. However, once there is a chemical agent like MOPS, ethanol or glycerin, or a mixture thereof, presented in the environment, the poison/toxic gene in the bacteria is then activated to manifest its effects.

DEFINITION, COMPOSITION AND APPLICATIONS

A. Definitions

To facilitate understanding of the invention, a number of terms are defined below:

Nucleic Acid: a polymer of deoxyribonucleic acid (DNA) or ribonucleic acid (RNA), either single or double stranded.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. A nucleoside containing at least one phosphate group bonded to the 3' or 5' position of the pentose is a nucleotide. DNA and RNA are consisted of different types of nucleotide units called deoxyribonucleotide and ribonucleotide, respectively.

Oligonucleotide: a molecule comprised of two or more monomeric units of DNA and/or RNA, preferably more than three, and usually more than ten. An oligonucleotide longer than 13 nucleotide monomers is also called polynucleotide. The exact size will depend on many factors, which in turn depends on the ultimate function or use of the oligonucleotide. The oligonucleotide may be generated in any manner, including chemical synthesis, DNA replication, RNA transcription, reverse transcription, or a combination thereof.

Nucleotide Analog: a purine or pyrimidine nucleotide that differs structurally from adenine (A), thymine (T), guanine (G), cytosine (C), or uracil (U), but is sufficiently similar to substitute for the normal nucleotide in a nucleic acid molecule.

Nucleic Acid Composition: a nucleic acid composition refers to an oligonucleotide or polynucleotide such as a DNA or RNA sequence, or a mixed DNA/RNA sequence, in either a single-stranded or a double-stranded molecular structure.

Gene: a nucleic acid composition whose oligonucleotide or polynucleotide sequence codes for an RNA and/or a polypeptide (protein). A gene can be either RNA or DNA. A gene may encode a non-coding RNA, such as small hairpin RNA (shRNA), microRNA (miRNA), rRNA, tRNA, snoRNA, snRNA, and their RNA precursors as well as derivatives. Alternatively, a gene may encode a protein-coding RNA essential for protein/peptide synthesis, such as messenger RNA (mRNA) and its RNA precursors as well as derivatives. In some cases, a gene may encode a protein-coding RNA that also contains at least a microRNA or shRNA sequence.

Primary RNA Transcript: an RNA sequence that is directly transcribed from a gene without any RNA processing or modification.

Precursor messenger RNA (pre-mRNA): primary RNA transcripts of a protein-coding gene, which are produced by eukaryotic type-II RNA polymerase (Pol-II) machineries in eukaryotes through an intracellular mechanism termed transcription. A pre-mRNA sequence contains a 5'-untranslated region (UTR), a 3'-UTR, exons and introns.

Intron: a part or parts of a gene transcript sequence encoding non-protein-reading frames, such as in-frame intron, 5'-UTR and 3'-UTR.

Exon: a part or parts of a gene transcript sequence encoding protein-reading frames (cDNA), such as cDNA for cellular genes, growth factors, insulin, antibodies and their analogs/homologs as well as derivatives.

Messenger RNA (mRNA): assembly of pre-mRNA exons, which is formed after intron removal by intracellular RNA splicing machineries (e.g. spliceosomes) and served as a protein-coding RNA for peptide/protein synthesis. The peptides/proteins encoded by mRNAs include, but not limited, enzymes, growth factors, insulin, antibodies and their analogs/homologs as well as derivatives.

Complementary DNA (cDNA): a single-stranded or double-stranded DNA that contains a sequence complementary to an mRNA sequence and does not contain any intronic sequence.

Sense: a nucleic acid molecule in the same sequence order and composition as the homologous mRNA. The sense conformation is indicated with a "+", "s" or "sense" symbol.

Antisense: a nucleic acid molecule complementary to the respective mRNA molecule. The antisense conformation is indicated as a "−" symbol or with an "a" or "antisense" in front of the DNA or RNA, e.g., "aDNA" or "aRNA".

Base Pair (bp): a partnership of adenine (A) with thymine (T), or of cytosine (C) with guanine (G) in a double stranded DNA molecule. In RNA, uracil (U) is substituted for thymine. Generally the partnership is achieved through hydrogen bonding. For example, a sense nucleotide sequence "5'-A-T-C-G-U-3'" can form complete base pairing with its antisense sequence "5'-A-C-G-A-T-3'".

5'-end: a terminus lacking a nucleotide at the 5' position of successive nucleotides in which the 5'-hydroxyl group of one nucleotide is joined to the 3'-hydroxyl group of the next nucleotide by a phosphodiester linkage. Other groups, such as one or more phosphates, may be present on the terminus.

3'-end: a terminus lacking a nucleotide at the 3' position of successive nucleotides in which the 5'-hydroxyl group of one nucleotide is joined to the 3'-hydroxyl group of the next nucleotide by a phosphodiester linkage. Other groups, most often a hydroxyl group, may be present on the terminus.

Template: a nucleic acid molecule being copied by a nucleic acid polymerase. A template can be single-stranded, double-stranded or partially double-stranded, depending on the polymerase. The synthesized copy is complementary to the template, or to at least one strand of a double-stranded or partially double-stranded template. Both RNA and DNA are synthesized in the 5' to 3' direction. The two strands of a nucleic acid duplex are always aligned so that the 5' ends of the two strands are at opposite ends of the duplex (and, by necessity, so then are the 3' ends).

Nucleic Acid Template: a double-stranded DNA molecule, double stranded RNA molecule, hybrid molecules such as DNA-RNA or RNA-DNA hybrid, or single-stranded DNA or RNA molecule.

Conserved: a nucleotide sequence is conserved with respect to a pre-selected (referenced) sequence if it non-randomly hybridizes to an exact complement of the pre-selected sequence.

Homologous or Homology: a term indicating the similarity between a polynucleotide and a gene or mRNA sequence. A nucleic acid sequence may be partially or completely homologous to a particular gene or mRNA sequence, for example. Homology may be expressed as a percentage determined by the number of similar nucleotides over the total number of nucleotides.

Complementary or Complementarity or Complementation: a term used in reference to matched base pairing between two polynucleotides (i.e. sequences of an mRNA and a cDNA) related by the aforementioned "base pair (bp)" rules. For example, the sequence "5'-A-G-T-3'" is complementary to the sequence "5'-A-C-T-3'", and also to "5'-A-C-U-3'". Complementation can be between two DNA strands, a DNA and an RNA strand, or between two RNA strands. Complementarity may be "partial" or "complete" or "total". Partial complementarity or complementation occurs when only some of the nucleic acid bases are matched according to the base pairing rules. Complete or total complementarity or complementation occurs when the bases are completely or perfectly matched between the nucleic acid strands. The degree of complementarity between nucleic acid strands has significant effects on the efficiency and strength of hybridization between nucleic acid strands.

This is of particular importance in amplification reactions, as well as in detection methods that depend on binding between nucleic acids. Percent complementarity or complementation refers to the number of mismatch bases over the total bases in one strand of the nucleic acid. Thus, a 50% complementation means that half of the bases were mismatched and half were matched. Two strands of nucleic acid can be complementary even though the two strands differ in the number of bases. In this situation, the complementation occurs between the portion of the longer strand corresponding to the bases on that strand that pair with the bases on the shorter strand.

Complementary Bases: nucleotides that normally pair up when DNA or RNA adopts a double stranded configuration.

Complementary Nucleotide Sequence: a sequence of nucleotides in a single-stranded molecule of DNA or RNA that is sufficiently complementary to that on another single strand to specifically hybridize between the two strands with consequent hydrogen bonding.

Hybridize and Hybridization: the formation of duplexes between nucleotide sequences which are sufficiently complementary to form complexes via base pairing. Where a primer (or splice template) "hybridizes" with target (template), such complexes (or hybrids) are sufficiently stable to serve the priming function required by a DNA polymerase to initiate DNA synthesis. There is a specific, i.e. non-random, interaction between two complementary polynucleotides that can be competitively inhibited.

Posttranscriptional Gene Silencing: a targeted gene knockout or knockdown effect at the level of mRNA degradation or translational suppression, which is usually triggered by either foreign/viral DNA or RNA transgenes or small inhibitory RNAs.

RNA Interference (RNAi): a posttranscriptional gene silencing mechanism in eukaryotes, which can be triggered by small inhibitory RNA molecules such as microRNA (miRNA), small hairpin RNA (shRNA) and small interfering RNA (siRNA). These small RNA molecules usually function as gene silencers, interfering with expression of intracellular genes containing either completely or partially complementarity to the small RNAs.

Gene Silencing Effect: a cell response after a gene function is suppressed, consisting but not limited of cell cycle attenuation, G0/G1-checkpoint arrest, tumor suppression, anti-tumorigenicity, cancer cell apoptosis, and a combination thereof.

Non-coding RNA: an RNA transcript that cannot be used to synthesize peptides or proteins through intracellular translation machineries. Non-coding RNA includes long and short regulatory RNA molecules such as microRNA (miRNA), small hairpin RNA (shRNA), small interfering RNA (siRNA) and double strand RNA (dsRNA). These regulatory RNA molecules usually function as gene silencers, interfering with expression of intracellular genes containing either completely or partially complementarity to the non-coding RNAs.

MicroRNA (miRNA): single-stranded RNAs capable of binding to targeted gene transcripts that have partial complementarity to the miRNA. MiRNA is usually about 17-27 oligonucleotides in length and is able to either directly degrade its intracellular mRNA target(s) or suppress the protein translation of its targeted mRNA, depending on the complementarity between the miRNA and its target mRNA. Natural miRNAs are found in almost all eukaryotes, functioning as a defense against viral infections and allowing regulation of gene expression during development of plants and animals.

Precursor MicroRNA (Pre-miRNA): hairpin-like single-stranded RNAs containing stem-arm and stem-loop regions for interacting with intracellular RNaseIII endoribonucleases to produce one or multiple microRNAs (miRNAs) capable of silencing a targeted gene or genes complementary to the microRNA sequence(s). The stem-arm of a pre-miRNA can form either a perfectly (100%) or a partially (mis-matched) hybrid duplexes, while the stem-loop connects one end of the stem-arm duplex to form a circle or hairpin-loop conformation. In the present invention, however, precursor of microRNA may also includes pri-miRNA.

Small interfering RNA (siRNA): short double-stranded RNAs sized about 18-27 perfectly base-paired ribonucleotide duplexes and capable of degrading target gene transcripts with almost perfect complementarity.

Small or short hairpin RNA (shRNA): single-stranded RNAs that contain a pair of partially or completely matched stem-arm nucleotide sequences divided by an unmatched loop oligonucleotide to form a hairpin-like structure. Many natural miRNAs are derived from hairpin-like RNA precursors, namely precursor microRNA (pre-miRNA).

Vector: a recombinant nucleic acid composition such as recombinant DNA (rDNA) capable of movement and residence in different genetic environments. Generally, another nucleic acid is operatively linked therein. The vector can be capable of autonomous replication in a cell in which case the vector and the attached segment is replicated. One type of preferred vector is an episome, i.e., a nucleic acid molecule capable of extrachromosomal replication. Preferred vectors are those capable of autonomous replication and expression of nucleic acids. Vectors capable of directing the expression of genes encoding for one or more polypeptides and/or non-coding RNAs are referred to herein as "expression vectors" or "expression-competent vectors". Particularly important vectors allow cloning of cDNA from mRNAs produced using a reverse transcriptase. A vector may contain components consisting of a viral or a type-II RNA polymerase (Pol-II or pol-2) promoter, or both, a Kozak consensus translation initiation site, polyadenylation signals, a plurality of restriction/cloning sites, a pUC origin of replication, a SV40 early promoter for expressing at least an antibiotic resistance gene in replication-competent prokaryotic cells, an optional SV40 origin for replication in mammalian cells, and/or a tetracycline responsive element. The structure of a vector can be a linear or circular form of single- or double-stranded DNA selected form the group consisting of plasmid, viral vector, transposon, retrotransposon, DNA transgene, jumping gene, and a combination thereof.

Promoter: a nucleic acid to which a polymerase molecule recognizes, perhaps binds to, and initiates RNA transcription. For the purposes of the instant invention, a promoter can be a known polymerase binding site, an enhancer and the like, any sequence that can initiate synthesis of RNA transcripts by a desired polymerase.

Eukaryotic Promoter: a sequence of nucleic acid motifs which are required for gene transcription and can be recognized by eukaryotic type II RNA polymerases (pol-2), pol-2 equivalent, and/or pol-2 compatible viral polymerases Type-II RNA Polymerase (Pol-II or pol-2) Promoter: a RNA promoter that is recognized and bound by eukaryotic type-II RNA polymerases (Pol-II or pol-2) which transcribe eukaryotic messenger RNAs (mRNAs) and/or microRNAs (miRNAs). For example, but not limited, a pol-2 promoter can be a mammalian RNA promoter or a cytomegaloviral (CMV) promoter.

Type-II RNA Polymerase (Pol-II or pol-2) Equivalent: an eukaryotic transcription machinery selected from the group consisting of mammalian type-II RNA polymerases (Pol-II or pol-2) and Pol-II compatible viral RNA polymerases.

Pol-II Compatible Viral Promoter: a viral RNA promoter capable of using the eukaryotic poi-2 or equivalent transcription machinery for its gene expression. For example, but not limited, a pol-2 compatible viral promoter can be a cytomegaloviral (CMV) promoter or a retroviral long terminal repeat (LTR) promoter.

Cistron: a sequence of nucleotides in a DNA molecule coding for an amino acid residue sequence and including upstream and downstream DNA expression control elements.

RNA Processing: a cellular mechanism responsible for RNA maturation, modification and degradation, including RNA splicing, intron excision, exosome digestion, nonsense-mediated decay (NMD), RNA editing, RNA processing, and a combination thereof.

Antibiotic Resistance Gene: a gene capable of degrading antibiotics selected from the group consisted of penicillin G, streptomycin, ampicillin (Amp), neomycin, G418, kanamycin, erythromycin, paromycin, phophomycin, spectromycin, tetracycline (Tet), doxycycline (Dox), rifapicin, amphotericin B, gentamycin, chloramphenicol, cephalothin, tylosin, and a combination thereof.

Restriction/Cloning Site: a DNA motif for restriction enzyme cleavage including but not limited to AatII, AccI, AflII/III, AgeI, ApaI/LI, AseI, Asp718I, BamHI, BbeI, BclI/II, BglII, BsmI, Bsp120I, BspHI/LU11I/120I, BsrI/BI/GI, BssHII/SI, BstBI/U1/XI, ClaI, Csp6I, DpnI, DraI/II, EagI, Ecl136II, EcoRI/RII/47III/RV, EheI, FspI, HaeIII, HhaI, HinPI, HindIII, HinfI, HpaI/II, KasI, KpnI, MaeII/III, MfeI, MluI, MscI, MseI, NaeI, NarI, NcoI, NdeI, NgoMI, NotI, NruI, NsiI, PmlI, Ppu10I, PstI, PvuI/II, RsaI, SacI/II, SalI, Sau3AI, SmaI, SnaBI, SphI, SspI, StuI, TaiI, TaqI, XbaI, XhoI, XmaI cleavage site.

Gene Delivery: a genetic engineering method selected from the group consisting of polysomal transfection, liposomal transfection, chemical transfection, electroporation, viral infection, DNA recombination, transposon insertion, jumping gene insertion, microinjection, gene-gun penetration, and a combination thereof.

Genetic Engineering: a DNA recombination method selected from the group consisting of DNA restriction and ligation, homologous recombination, transgene incorporation, transposon insertion, jumping gene integration, retroviral infection, and a combination thereof.

Cell Cycle Regulator: a cellular gene involved in controlling cell division and proliferation rates, consisting but not limited of CDK2, CDK4, CDK6, cyclins, BMI-1, p14/p19Arf, p15Ink4b, p16Ink4a, p18Ink4c, p21Cip1/Waf1, and p27Kip1, and a combination thereof.

Tumor Suppression: a cellular anti-tumor and anti-cancer mechanism consisting but not limited of cell cycle attenuation, G0/G1-checkpoint arrest, tumor suppression, anti-tumorigenicity, cancer cell apoptosis, and a combination thereof.

Targeted Cell: a single or a plurality of human cells selected from the group consisting of a somatic cell, a tissue, a stem cell, a germ-line cell, a teratoma cell, a tumor cell, a cancer cell, and a combination thereof.

Cancerous Tissue: a neoplastic tissue derived from the group consisting of skin cancer, prostate cancer, breast cancer, liver cancer, lung cancer, brain tumor/cancer, lymphoma, leukemia and a combination thereof.

Transcription Inducer: a chemical agent that can stimulate and/or enhance RNA transcription from a gene. A transcription inducer contains, but not limited, a chemical structure similar to 3-morpholinopropane-1-sulfonic acid (MOPS), ethanol or glycerin, or a mixture thereof.

Antibody: a peptide or protein molecule having a pre-selected conserved domain structure coding for a receptor capable of binding a pre-selected ligand.

Pharmaceutical or therapeutic Application: a biomedical utilization and/or apparatus useful for stem cell generation, stem cell research and/or therapy development, cancer therapy, disease treatment, wound healing treatment, high-yield production of drug and/or food supplies, and a combination thereof.

B. Compositions and Applications

A composition and its use for inducing RNA and/or protein expression in prokaryotes, comprising: (a) at least a chemical agent containing a structure similar to 3-morpholinopropane-1-sulfonic acid (MOPS), ethanol or glycerin, or a mixture thereof; and (b) a plurality of prokaryotic cells that contain at least a gene mediated by a eukaryotic pol-2 promoter-driven or a pol-2 compatible viral promoter-driven expression mechanism; wherein (a) and (b) are mixed together under a condition to induce the expression of said gene, so as to generate the RNA and/or protein products of said gene.

Alternatively, the present invention is an inducible gene expression composition using chemical agents to stimulate eukaryotic RNA promoter-driven transcription in prokaryotes. An inducible gene expression composition, comprising (a) at least a chemical agent containing a structure similar to 3-morpholinopropane-1-sulfonic acid (MOPS), ethanol or glycerin, or a mixture thereof; and (b) a plurality of prokaryotic cells that contain at least a gene mediated by a eukaryotic pol-2 promoter-driven or a pol-2 compatible viral promoter-driven expression mechanism; wherein (a) and (b) are mixed together under a condition to induce the expression of said gene.

In principle, the present invention provides a novel composition design and its applicable strategy for inducing a quick adaptation of prokaryotes to use eukaryotic pol-2 promoters for directly expressing RNAs and/or proteins of interest without the need of changing to error-prone prokaryotic promoters or growing laborious and costly hybridomas or mammalian cells.

Preferably, said prokaryote is a bacterial cells in particular, *Escherichia coli* (*E. coli*), and said chemical agent is 3-morpholinopropane-1-sulfonic acid (MOPS), ethanol or glycerin, or a mixture thereof. Also preferably, said eukaryotic RNA promoter is either a eukaryotic pol-2 promoter, such as EF1alpha, or a pol-2 compatible viral promoter, such as cytomegaloviral (CMV) promoter or retroviral long terminal repeat (LTR) promoter. The gene mediated by said eukaryotic RNA promoter is coded for either a non-coding or a protein-coding RNA transcript, or both, selected from the group consisted of microRNA (miRNA), small hairpin RNA (shRNA), small interfering RNA (siRNA), messenger RNA (mRNA), their precursors and homologs, and a combination thereof. The peptide/protein generated by the present invention is translated from the above protein-coding mRNA transcripts and may be selected from, but not limited to, the group consisted of enzyme, growth factor, antibody, insulin, botulinum toxin (botox), a functional protein and its homologs/analogs, and a combination thereof. Preferably, said condition for inducing the expression of said gene is a bacterial culturing condition in Luria-Bertani (LB) broth at 37° C. with the addition of said chemical agents.

Recap of the Drawing Illustrations:

Referring particularly to the drawings for the purpose of illustration only and not limitation, there is illustrated:

Referring to FIGS. 1A and 1B, there is shown an inducible pol-2 promoter-driven gene expression composition (A) and its mechanisms (B) for RNA transcript and protein production in prokaryotes and eukaryotes and microRNA (miRNA) production in eukaryotes. For demonstrating the present invention, pLenti-EF1alpha-RGFP-miR302 is served as an example composition to transform competent *E. coli* DH5alpha cells for producing RGFP mRNA and protein as well as miR-302 miRNA and/or precursors thereof under the control of MOPS, glycerin and/or ethanol induction. The pLenti-EF1alpha-RGFP-miR302 is a lentiviral plasmid vector that is designed to expresses various miRNAs/shRNAs, mRNAs and/or proteins/peptides in both prokaryotes and eukaryotes. According to the disclosed mechanism (B), it is possible for an ordinary skill in the art to use any microRNA/shRNA in place miR-302 or any mRNA/protein in place of RGFP as taught in the present invention. Black arrows indicate the pathways occurring in both prokaryotic and eukaryotic cells, while blank arrows indicate the steps only occurring in the eukaryotic cells.

Referring to FIG. 2, there is depicted the results of bacterial culture broths treated with (left) or without (right) the mixture of 0.1% (v/v) MOPS and 0.05% (v/v) glycerin. The *E. coli* bacteria have been transformed by pLenti-EF1alpha-RGFP-miR302 before treatments.

Referring to FIG. 3, there is shown the results of different bacterial pellets after treated with 0.1% (v/v) MOPS. The *E. coli* bacteria have been transformed by either pLVX-Gm-miR302+367 (green) or pLenti-EF1alpha-RGFP-miR302 (red) before MOPS treatment.

Referring to FIG. 4, there is shown the inducibility of different chemicals for inducing pol-2 promoter-driven gene expression in competent *E. coli* DH5alpha cells. Among all chemicals tested in the present invention, the top three most potent inducers are MOPS, glycerin and ethanol. The chemical concentration used can be ranged from 0.001% to 4%, most preferably, from 0.01 to 1%.

Referring to FIG. 5, there is shown the Western blotting results of red RGFP protein expression induced by MOPS, glycerin and ethanol, respectively. Bacterial RuvB protein is used as a house-keeping standard to normalize the RGFP expression. Protein extraction from blank *E. coli* DH5alpha cells, i.e. transformed no vectors, serves as a negative control.

Referring to FIG. 6, there is shown the Northern blotting results of miR-302 and its pre-miRNA cluster expression induced by MOPS, glycerin and ethanol, respectively. RNA extraction from blank *E. coli* DH5alpha cells serves as a negative control.

Referring to FIG. 7, there is shown iPS cell generation using miR-302 and/or pre-miR-302 isolated from bacterial extracts (BE), which is confirmed by Northern blot analysis as shown in FIG. 6. As previously reported, miR-302-reprogrammed iPS cells (mirPSCs) form sphere-like cell colonies and express strong Oct4, a standard ESC marker.

Figure 8:
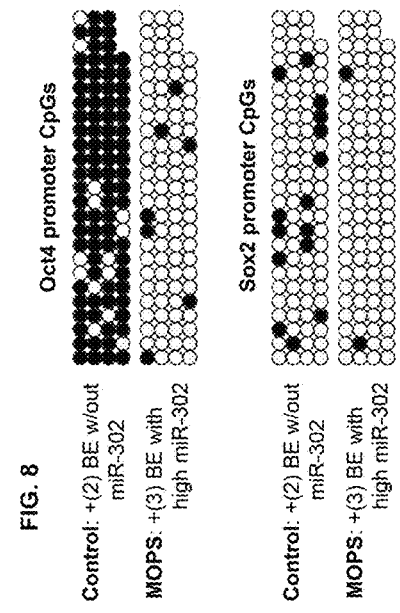
FIG. 8 shows the global DNA demethylation of Oct4 and Sox2 gene promoters induced by the miR-302 and/or pre-miR-302 isolated from bacterial extracts (BE).

Referring to FIG. 8, there is shown the global DNA demethylation of Oct4 and Sox2 gene promoters induced by the miR-302 and/or pre-miR-302 isolated from bacterial extracts (BE), which is confirmed by Northern blot analysis as shown in FIG. 6. As demonstrated by Simonsson and Gurdon (*Nat Cell Biol.* 6, 984-990, 2004), both signs of global DNA demethylation and Oct4 expression are required for somatic cell reprogramming.

Referring to FIGS. 9A-9C and 10A-10B, there is shown in vitro tumorigenicity assays of various tumor/cancer cells in response to miR-302 and/or pre-miR-302 treatment. The cells obtained after miR-302 and/or pre-miR-302 treatment are labeled as mirPS cells, including breast cancer-derived mirPS-MCF7, liver cancer-derived mirPS-HepG2, and embryonal teratocarcinoma-derived mirPS-Tera2 cells. FIGS. 9A-9B: Changes of cell morphology and cell cycle rate before and after miR-302 and/or pre-miR-302 treatment. Each cell DNA content respective to cell cycle stages was shown by a chart of flow cytometry analysis above the cell morphology (n=3, p<0.01). FIG. 9C: Bar charts of flow cytometry analyses showing the dose-dependent miR-302 and/or pre-miR-302 effect on the changes of mitotic (M phase) and dormant (G0/G1 phase) cell populations of various treated tumor/cancer cells. FIG. 10A: Functional analysis of miR-302-suppressed tumor invasion in Matrigel chambers (n=4, p<0.05). FIG. 10B: Comparison of cell adhesion to the hBMEC monolayer before and after miR-302 and/or pre-miR-302 treatment (n=4, p<0.05).

Referring to FIGS. 11A-11C, there is shown in vivo tumorigenicity assays of embryonal teratocarcinoma Tera-2 cells in response to either the whole miR-302 familial cluster (Tera2+mir-302s) or antisense miR-302d only (Tera2+mir-302d*) treatment (n=3, p<0.05). Embryonal teratocarcinoma often contains various tumor/cancer cells derived from all three embryonic germ layers (i.e. ectoderm, mesoderm and endoderm), which represent a mixed neoplastic tissue useful for testing anti-tumor/cancer drugs. (A) Morphological evaluation of average tumor sizes three weeks after the in-situ injection (post-is). All tumors were localized in the original implant sites (black arrows). No signs of cachexia or tumor metastasis were observed in all tested mice. (B) Northern and western blot analyses and (C) Immunohistochemical staining analyses of the in vivo miR-302 effect on the expression patterns of core reprogramming factors Oct3/4-Sox2-Nanog and miR-302-targeted G1-checkpoint regulators CDK2, cyclins D1/D2 and BMI-1 as well as p16Ink4a and p14Arf.

Referring to FIG. 12, there is shown the results of an in-vivo wound healing trial using microRNA miR-302 and/or pre-miR-302 containing ointment to treat skin open wounds in mice. The skin wounds of miR-302 and/or pre-miR-302-treated mice were at least twice larger than those of control mice treated with only blank ointment or other microRNA (miR-HA). The trial results clearly demonstrated that miR-302 and/or pre-miR-302 treatments significantly enhanced the speed of wound healing over two times faster than all other treatments and controls. Moreover, miR-302 and/or pre-miR-302-treated wound healing area showed normal hair regrowth and left no scar while other treatments resulted in minor scars with no hair (indicated by black arrow).

EXAMPLES

1. Bacterial Cell Culture and Chemical Treatments

Competent *E. coli* DH5alpha cells are acquired from the z-competent *E. coli* transformation kit (Zymo Research, Irvine, Calif.) and transformed by mixing with 5 μg of a desired plasmid vector such as pLVX-Gm-miR302+367 or pLenti-EF1alpha-RGFP-miR302. Non-transformed bacterial cells are normally grown in Luria-Bertani (LB) broth supplemented with 10 mM $MgSO_4$ and 0.2 mM glucose at 37° C. with frequent agitation at 170 rpm, whereas the transformed bacterial cells are cultivated in the above LB broth further supplemented with additional 100 ampicillin. For chemical induction, 0.5 to 2 ml of MOPS, glycerin, and ethanol, respectively or in combination, is added into 1 litter LB broth supplemented with 10 mM $MgSO_4$ and 0.2 mM glucose in the presence of 100 μg/ml ampicillin. For negative control, the transformed bacterial cells are cultivated in the above ampicillin-supplemented LB broth but without out adding any chemical inducer.

2. Human Cell Culture and MicroRNA Transfection

Human primary epidermal skin cells (hpESCs) are isolated and dissociated from a minimum of 2 cubic mm by 4 mg/ml collagenase I digestion at 37° C. for 35 min in fresh RPMI 1640 medium supplemented with 20% FBS. For culturing keratinocytes, the isolated cells are cultivated in EpiLife serum-free cell culture medium supplemented with human keratinocyte growth supplements (HKGS, Invitrogen, Carlsbad, Calif.) in the absence of antibiotics at 37° C. under 5% $CO_2$. Culture cells are passaged at 50%-60% confluency by exposing cells to trypsin/EDTA solution for 1 min and rinsing once with phenol red-free DMEM medium (Invitrogen), and the detached cells are replated at 1:10 dilution in fresh EpiLife medium with HKGS supplements. Human cancer/tumor cell lines MCF7, HepG2 and Tera-2 were obtained from the American Type Culture Collection (ATCC, Rockville, Md.) and maintained according to manufacturer's suggestions. For microRNA transfection, 15 μg of isolated miR-302 and/or precursor thereof is dissolved in 1 ml of fresh EpiLife medium and mixed with 50 μl of X-tremeGENE HP DNA transfection reagent. After 10 min incubation, the mixture is added into a 100-mm cell culture dish containing 50%-60% confluency of hpESCs or the cancer/tumor cells, respectively. The medium is replaced by fresh EpiLife medium with HKGS supplements or the conditioned medium suggested by ATCC 12 to 18 hours later. This transfection procedure may be repeated 3 to 4 times every three-four days to increase transfection efficiency. After cell morphology become sphere-like, the cells (mirPSCs) are grown and passaged in knockout DMEM/F-12 medium (Invitrogen) supplemented with 20% knockout serum, 1% MEM nonessential amino acids, 100 μM β-mercaptoethanol, 1 mM GlutaMax, 1 mM sodium pyruvate, 10 ng/ml bFGF, 10 ng/ml FGF-4, 5 ng/ml LIF, 100 IU/ml penicillin/100 μg/ml streptomycin, 0.1 μM A83-01, and 0.1 μM valproic acid (Stemgent, San Diego, Calif.), at 37° C. under 5% $CO_2$.

3. Protein Extraction and Western Blot Analysis

Cells ($10^6$) are lysed with a CelLytic-M lysis/extraction reagent (Sigma) supplemented with protease inhibitors, Leupeptin, TLCK, TAME and PMSF, following the manufacturer's suggestion. Lysates are centrifuged at 12,000 rpm for 20 min at 4° C. and the supernatant is recovered. Protein concentrations are measured using an improved SOFTmax protein assay package on an E-max microplate reader (Molecular Devices, CA). Each 30 μg of cell lysate are added to SDS-PAGE sample buffer under reducing (+50 mM DTT) and non-reducing (no DTT) conditions, and boiled for 3 min before loading onto a 6~8% polyacrylamide gel. Proteins are resolved by SDS-polyacrylamide gel electrophoresis (PAGE), electroblotted onto a nitrocellulose membrane and incubated in Odyssey blocking reagent (Li-Cor Biosciences, Lincoln, NB) for 2 hours at room temperature. Then, a primary antibody is applied to the reagent and incubated the mixture at 4° C. Primary antibodies include Oct3/4 (Santa Cruz Biotechnology, Santa Cruz, Calif.), Sox2 (Santa Cruz), Nanog (Santa Cruz), CDK2 (Santa Cruz), cyclin D1 (Santa Cruz), cyclin D2 (Abcam), BMI-1 (Santa Cruz), keratin 16 (Abcam), β-actin (Chemicon, Temecula, Calif.), RuvB (Santa Cruz) and RGFP (Clontech). After overnight, the membrane is rinsed three times with TBS-T and then exposed to goat anti-mouse IgG conjugated secondary antibody to Alexa Fluor 680 reactive dye (1:2,000; Invitrogen-Molecular Probes), for 1 hour at the room temperature. After three additional TBS-T rinses, fluorescent scanning of the immunoblot and image analysis are conducted using Li-Cor Odyssey Infrared Imager and Odyssey Software v.10 (Li-Cor).

4. RNA Extraction and Northern Blot Analysis

Total RNAs (10 μg) are isolated with a mirVana™ miRNA isolation kit (Ambion, Austin, Tex.), fractionated by either 15% TBE-urea polyacrylamide gel or 3.5% low melting point agarose gel electrophoresis, and electroblotted onto a nylon membrane. Detection of miR-302 and/or pre-miR-302 is performed with a [LNA]-DNA probe (5'-[TCACTGAAAC] ATGGAAGCAC TTA-3') (SEQ-.ID.NO.1) probe. The probe has been purified by high-performance liquid chromatography (HPLC) and tail-labeled with terminal transferase (20 units) for 20 min in the presence of [$^{32}$P]-dATP (>3000 Ci/mM, Amersham International, Arlington Heights, Ill.).

5. Plasmid Amplification and Plasmid DNA/Total RNA Extraction

Competent *E. coli* DH5alpha cells treated with plasmid transformation (from Example 1) are cultivated overnight in LB broth supplemented with 10 mM $MgSO_4$ and 0.2 mM glucose at 37° C. with frequent agitation at 170 rpm. For inducing eukaryotic promoter-driven RNA and/or protein production, 0.5 to 2 ml of MOPS, glycerin, and/or ethanol is added into every 1 litter of LB broth for the above bacterial cultivation and amplification. All amplified plasmid DNAs and expressed mRNAs/microRNAs are isolated together using a HiSpeed plasmid purification kit (Qiagen, Valencia, Calif.), following the manufacturer's protocol but with a minor modification that RNase A is not added into the P1 buffer. The final extracted products containing both plasmids and mRNAs/microRNAs are dissolved in DEPC-treated $ddH_2O$ and stored at −80° C. before use. For purifying only the amplified plasmid vectors, RNase A is added into the P1 buffer and the extraction procedure is performed following the manufacturer's protocol.

6. MicroRNA and mRNA Isolation/Purification

Total RNAs isolated from the above Example 5 are further purified using a mirVana™ miRNA isolation kit (Ambion, Austin, Tex.), following the manufacturer's protocol. The final products are dissolved in DEPC-treated $ddH_2O$ and stored at −80° C. before use. Because bacterial RNAs are degraded very fast (a few hours) in nature while eukaryotic poly-A RNAs (mRNAs) and hairpin-like microRNA precursors (pre-miRNA or pri-miRNA) remain relatively stable at 4° C. (half-life up to 3-4 days), we can use this difference to acquire pure mRNAs and/or pre-miRNAs for further applications. For example, RGFP mRNA can be used to identify the transfected cells, while pre-miR-302s are used to reprogram somatic cells to ESC-like iPS cells. The purified pre-miR-302s can also be added into stem cell culture medium to facilitate and maintain the reprogramming process.

7. Immunostaining Assay

Embedding, sectioning and immunostaining tissue samples are performed as reported (Lin et al., RNA 2008). Primary antibodies include Oct4 (Santa Cruz), Sox2 (Santa Cruz), Nanog (Santa Cruz), and RGFP (Clontech). Fluorescent dye-labeled goat anti-rabbit or horse anti-mouse antibody is used as the secondary antibody (Invitrogen-Molecular Probes). Positive results are examined and analyzed at 100× or 200× magnification under a fluorescent 80i microscopic quantitation system with a Metamorph imaging program (Nikon).

8. Bisulfite DNA Sequencing

Genomic DNAs are isolated from about two million cells using a DNA isolation kit (Roche, Indianapolis, Iowa) and 1 µg of the isolated DNAs are further treated with bisulfite (CpGenome DNA modification kit, Chemicon, Temecula, Calif.), according to the manufacturers' suggestions. The treatment with bisulfite converts all unmethylated cytosine to uracil, while methylated cytosine remains as cytosine. For bisulfite DNA sequencing analyses, we amplify the promoter regions of Oct4 and Nanog with PCR. Primers include 5'-GAGGCTGGAG CAGAAGGATT GCTTTGG-3'(SEQ.ID.NO.2) and 5'-CCCTCCTGAC CCATCACCTC CAC-CACC-3'(SEQ.ID.NO.3) for Oct4, and 5'-TGGTTAGGTT GGTTTTAAAT TTTTG-3' (SEQ.ID.NO.4) and 5'-AAC-CCACCCT TATAAATTCT CAATTA-3'(SEQ.ID.NO.5) for Nanog. The bisulfite-modified DNAs (50 ng) are first mixed with the primers (total 100 pmole) in 1×PCR buffer, heated to 94° C. for 2 min, and immediately cooled on ice. Next, 25 cycles of PCR are performed as follows: 94° C. for 1 min and 70° C. for 3 min, using an Expand High Fidelity PCR kit (Roche). The amplified DNA product with a correct size is further fractionized by 3% agarose gel electrophoresis, purified with a gel extraction filter (Qiagen), and then used in DNA sequencing. A detailed profile of the DNA methylation sites is then generated by comparing the unchanged cytosine in the converted DNA sequence to the unconverted one.

9. Cell Invasion Assay

Chamber inserts (12-µm pore size, Chemicon) were coated with 200 µg/ml of Matrigel alone or supplemented with 20% FBS in phenol red-free-DMEM with 1% L-glutamine and dried overnight under sterile conditions. Cells were harvested, washed, and resuspended in phenol red-free-DMEM to give a final cell density of $1\times10^5$ cells/ml. Five hundred microliters of the resulting cell suspension was then dispensed into the top chamber whereas DMEM conditioned medium (1.5 ml) was added to the bottom chamber to create a chemotactic gradient. Invasion was measured after overnight incubation at 37° C. for 16 hours. Top chambers were wiped with cotton wool, and invading cells on the underside of the membrane were fixed in 100% methanol for 10 min, air dried, stained in cresyl violet for 20 min, and gently rinsed in water. When dry, the cresyl violet stain on membranes was eluted using a 100% ethanol/0.2 M NaCitrate (1:1) wash for 20 min and absorbance read at 570 nm using a Precision Microplate Reader (Molecular Dynamics). The percentage of invading cells was calculated by comparison of absorbance in test samples against absorbance determined on membrane inserts that were not wiped (total cells). The result was shown in FIG. 10A.

10. Cell Adhesion Assay

Cell Adhesion assay was performed as reported (Lin et al., Cancer Res. 2010). Human bone marrow endothelial cells (hBMECs) were seeded at a density of $1\times10^5$ cells/ml in 96-well plates and washed with adhesion medium [RPMI 1640/0.1% BSA/20 mM HEPES (pH7.4)] before assays. Tested cells were trypsinized (tumor/cancer cells) or collagenase-digested (mirPS cells), washed in sterile saline, and resuspended at $1\times10^6$ cells/ml in PBS with 10 µM fura-4 acetoxymethyl ester (fluorescent probe, Sigma) for 1 hour at 37° C. in the dark. The cells were then pelleted, washed in serum-free medium containing 1% (v/v) of probenecid (100 mM) and incubated for 20 min in adhesion medium at 37° C. in the dark to activate the intracellular fluorescent probe. After that, $10^5$ cells (in 300-µl cell suspension/well) were added to the confluent hBMEC endothelial monolayer and incubated for 50 min at 37° C. Non-adherent cells were removed using 2×250 µl washes of adhesion medium. Plates were read in a fluorescent plate reader (Molecular Dynamics) at 37° C. using an excitation wavelength of 485 nm and an emission wavelength of 530 nm. The result was shown in FIG. 10B.

11. Implantation and Teratoma Formation

Approximately 5-10 mirPS cell-derived embryoid bodies (4- to 8-cell-stage) were suspended in 50 µl of a mixture of DMEM and Matrigel (2:1), followed by implantation into the uterus of a 6-week-old female pseudopregnant immunocompromised SCID-beige mouse. The pseudopregnant mice were prepared by intraperitoneal injection of 1 IU human menopausal gonadotrophin (HMG) for two days and then human chorionic gonadotrophin (hCG) for one more day. The mice were anesthetized with 2.5% Avertin solution, 0.4 ml per mouse during implantation. Xenografted masses were monitored 3-4 weeks after the implantation or when the sizes were grown to over 100 $mm^3$. Cysts/teratomas were dissected and the volumes were calculated using the formula (length×$width^2$)/2. Cyst/teratoma lesions were counted, weighed and subjected to further histological analysis. Formation of teratoma-like tissue cysts was usually observed at approximately 2.5-week post-implantation. The result was shown in FIG. 11A.

12. In Vivo Tumorigenicity Assay

We xenografted Tera-2 cells ($2\times10^6$ cells in a total volume of 100 µl Matrigel-PBS) into the flanks (e.g. right hind limb) of eight-week-old male mice (BALB/c nu/nu strain). Tumors were monitored weekly and in situ injection of either pre-miR-302s or pre-miR-302-encoding plasmid vectors, e.g. pCMV-miR302s vector or pCMV-miR302d*, was conducted one week after the Tera-2 xenograft. Five treatments (three-day intervals for each treatment) of 2 µg PEI-formulated pCMV-miR302s or pCMV-miR302d* vector (total 10 µg) per g mouse weight were performed. In vivo-jetPEI Delivery Reagent (Polyplus-transfection Inc., New York, N.Y.) was used as the manufacturer's suggestion. Samples were collected either three weeks post injection or when untreated tumors grew to an average size of approximately 100 $mm^3$. Major organs, such as the blood, brain, heart lung, liver, kidney and spleen, and the xenografts were removed for histological evaluation of tumor lesions and immunoreactive cytotoxicity. Tumor formation was monitored by palpation and tumor volume was calculated using the formula (length×width$^2$)/2. Tumor lesions were counted, dissected, weighed, and subjected to histological examination using H&E and immunostaining assays. Histological examination showed no detectable tissue lesions in brain, heart, lung, liver, kidney and spleen. The results were shown in FIGS. 11A and 11C.

13. In Vivo Wound Healing Test

The pre-miR-302s and their related plasmid vectors were amplified as described in Examples 1 and 5 and extracted as described in Examples 5 and 6. Then, the isolated pre-miR-302s and their related plasmid vectors were mixed with a pre-prepared ointment base containing cocoa butter, cottonseed oil, olive oil, sodium pyruvate, and white petrolatum. The concentration of miR-302 precursors and vectors in the prepared ointment base is 10 μg/mL. Skin open wounds were generated by scalpel dissection; approximately 0.5-cm for control and 1.0-cm for treated mice. Ointment (about 0.3 mL) was directly applied on the wound and covered the whole wounded area. Then, the treated area was further sealed by liquid bandage.

14. Statistic Analysis

Any change over 75% of signal intensity in the analyses of immunostaining, western blotting and northern blotting is considered as a positive result, which in turn is analyzed and presented as mean±SE. Statistical analysis of data is performed by one-way ANOVA. When main effects are significant, the Dunnett's post-hoc test is used to identify the groups that differ significantly from the controls. For pairwise comparison between two treatment groups, the two-tailed student t test is used. For experiments involving more than two treatment groups, ANOVA is performed followed by a post-hoc multiple range test. Probability values of p<0.05 is considered significant. All p values are determined from two-tailed tests.

Sequence Listing:
(1) GENERAL INFORMATION:
   (iii) NUMBER OF SEQUENCES: 5
(2) INFORMATION FOR SEQ ID NO:1:
   (i) SEQUENCE CHARACTERISTICS:
     (A) LENGTH: 23 base pairs
     (B) TYPE: nucleic acid
     (C) STRANDEDNESS: single
     (D) TOPOLOGY: linear
   (ii) MOLECULE TYPE: other nucleic acid
     (A) DESCRIPTION: /desc="synthetic"
   (iii) HYPOTHETICAL: NO
   (iv) ANTI-SENSE: YES
   (xi) SEQUENCE DESCRIPTION: SEQ ID NO:1: TCACTGAAAC ATGGAAGCAC TTA
(2) INFORMATION FOR SEQ ID NO:2:
   (i) SEQUENCE CHARACTERISTICS:
     (A) LENGTH: 27 base pairs
     (B) TYPE: nucleic acid
     (C) STRANDEDNESS: single
     (D) TOPOLOGY: linear
   (ii) MOLECULE TYPE: other nucleic acid
     (A) DESCRIPTION: /desc="synthetic"
   (iii) HYPOTHETICAL: NO
   (iv) ANTI-SENSE: NO
   (xi) SEQUENCE DESCRIPTION: SEQ ID NO:2: GAGGCTGGAG CAGAAGGATT GCTTTGG
(2) INFORMATION FOR SEQ ID NO:3:
   (i) SEQUENCE CHARACTERISTICS:
     (A) LENGTH: 27 base pairs
     (B) TYPE: nucleic acid
     (C) STRANDEDNESS: single
     (D) TOPOLOGY: linear
   (ii) MOLECULE TYPE: other nucleic acid
     (A) DESCRIPTION: /desc="synthetic"
   (iii) HYPOTHETICAL: NO
   (iv) ANTI-SENSE: NO
   (xi) SEQUENCE DESCRIPTION: SEQ ID NO:3: CCCTCCTGAC CCATCACCTC CACCACC
(2) INFORMATION FOR SEQ ID NO:4:
   (i) SEQUENCE CHARACTERISTICS:
     (A) LENGTH: 25 base pairs
     (B) TYPE: nucleic acid
     (C) STRANDEDNESS: single
     (D) TOPOLOGY: linear
   (ii) MOLECULE TYPE: other nucleic acid
     (A) DESCRIPTION: /desc="synthetic"
   (iii) HYPOTHETICAL: NO
   (iv) ANTI-SENSE: NO
   (xi) SEQUENCE DESCRIPTION: SEQ ID NO:4: TGGTTAGGTT GGTTTTAAAT TTTTG
(2) INFORMATION FOR SEQ ID NO:5:
   (i) SEQUENCE CHARACTERISTICS:
     (A) LENGTH: 25 base pairs
     (B) TYPE: nucleic acid
     (C) STRANDEDNESS: single
     (D) TOPOLOGY: linear
   (ii) MOLECULE TYPE: other nucleic acid
     (A) DESCRIPTION: /desc="synthetic"
   (iii) HYPOTHETICAL: NO
   (iv) ANTI-SENSE: NO
   (xi) SEQUENCE DESCRIPTION: SEQ ID NO:5: AACCCACCCT TATAAATTCT CAATTA

ADVANTAGES AND CLAIMS

The advantages of the present invention include: first, cost-effective production due to the fast growth of bacteria; second, easy handling because of no need for culturing dedicate hybridomas or mammalian cells; third, high product quality in view of the pol-2 promoter-like transcription and improved reading fidelity of the prokaryotic transcription machinery; fourth, industrial level bulk production for desired RNAs and their related peptides/proteins as well as the introduced plasmid vectors all at once in the bacteria; and last, multiple task capacity in that the desired RNAs and proteins can be separately isolated and purified from the bacterial extracts and/or lysates for further applications. Therefore, taken together, an inducible method for producing RNAs (i.e. messenger RNAs and microRNAs) and/or peptides/proteins (i.e. antibodies, growth factors and enzymes) using eukaryotic RNA promoter-driven transcription in prokaryotic cells is highly desirable.

It will be apparent to those skilled in the art that various modification and variations can be made in the method and related apparatus of the present invention without departing from the spirit or scope of the invention. Thus, it is intended that the present invention cover modifications and variations that come within the scope of the appended claims and their equivalents.

SEQUENCE LISTING

<160> NUMBER OF SEQ ID NOS: 5

<210> SEQ ID NO 1
<211> LENGTH: 23
<212> TYPE: DNA
<213> ORGANISM: Artificial Sequence
<220> FEATURE:
<223> OTHER INFORMATION: Synthetic oligonucleotides

<400> SEQUENCE: 1
tcactgaaac atggaagcac tta                                                23

<210> SEQ ID NO 2
<211> LENGTH: 27
<212> TYPE: DNA
<213> ORGANISM: Artificial Sequence
<220> FEATURE:
<223> OTHER INFORMATION: Primer

<400> SEQUENCE: 2
gaggctggag cagaaggatt gctttgg                                            27

<210> SEQ ID NO 3
<211> LENGTH: 27
<212> TYPE: DNA
<213> ORGANISM: Artificial Sequence
<220> FEATURE:
<223> OTHER INFORMATION: Primer

<400> SEQUENCE: 3
ccctcctgac ccatcacctc caccacc                                            27

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
tggttaggtt ggttttaaat ttttg                                              25

<210> SEQ ID NO 5
<211> LENGTH: 26
<212> TYPE: DNA
<213> ORGANISM: Artificial Sequence
<220> FEATURE:
<223> OTHER INFORMATION: Primer

<400> SEQUENCE: 5
aacccaccct tataaattct caatta                                             26

What is claimed is:

1. A composition for regulating eukaryotic elongation factor-1 alpha (EF1alpha) promoter-driven gene expression in prokaryotes, comprising:
   (a) at least a chemical agent capable of inducing or enhancing eukaryotic EF1alpha promoter-driven gene expression in prokaryotic cells, wherein said chemical agent containing a structure of 3-morpholinopropane-1-sulfonic acid (MOPS); and
   (b) a plurality of prokaryotic cells, said plurality of prokaryotic cells containing at least a gene mediated by a eukaryotic EF1alpha promoter-driven expression mechanism and wherein said gene encodes at least a hairpin-like structure in its 5'-untranslated region (5'-UTR) for being expressed in prokaryotes;
   wherein (a) and (b) are mixed together under a condition to induce the eukaryotic EF1alpha promoter-driven gene expression of said gene in said prokaryotic cells; wherein said condition is in Luria-Bertani (LB) broth.

2. The composition as defined in claim 1, wherein each one of said prokaryotic cells has at least an inducible gene expression composition.

3. The composition as defined in claim 2, wherein said gene is located in a plasmid vector containing at least a eukaryotic EF1alpha promoter.

4. The composition as defined in claim 1, wherein said gene encodes at least a non-coding RNA and a protein-coding RNA.

5. The composition as defined in claim 4, wherein said non-coding RNA is a small hairpin RNA.

6. The composition as defined in claim 4, wherein said protein-coding RNA further encodes a red fluorescent protein (RGFP).

7. The composition as defined in claim 4, wherein said protein-coding RNA contains 30% to 100% homology to a cDNA sequence of a eukaryotic gene.

8. The composition as defined in claim 4, wherein said non-coding RNA or said protein-coding RNA is isolatable from said prokaryotes.

9. The composition as defined in claim 1, wherein said gene encodes at least a protein.

10. The composition as defined in claim 4, wherein a protein transcribed from said protein-coding RNA contains at least a peptide sequence.

11. The composition as defined in claim 10, wherein said protein or said peptide is isolatable from said prokaryotes.

12. The composition as defined in claim 4, wherein a protein transcribed from said protein-coding RNA is an enzyme.

13. The composition as defined in claim 1, wherein said prokaryotic cells are bacterial cells.

14. The composition as defined in claim 1, wherein said prokaryotic cells are *Escherichia coli* (*E. coli*).

15. The composition as defined in claim 1, wherein said chemical agent is a transcription inducer for inducing RNA expression of said gene encoding at least the hairpin-like structure in said prokaryotic cells.

16. The composition as defined in claim 1, wherein said chemical agent in said condition has a v/v concentration of 0.01% to 1%.

17. The composition as defined in claim 4, wherein said non-coding RNA is useful for pharmaceutical or therapeutic application.

18. The composition as defined in claim 4, wherein said protein-coding RNA is useful for pharmaceutical or therapeutic application.

19. The composition as defined in claim 4, wherein said non-coding RNA is a precursor of microRNA.

20. The composition as defined in claim 19, wherein said precursor of microRNA is a precursor of miR-302.

21. The composition as defined in claim 4, wherein a protein transcribed from said protein-coding RNA is useful for pharmaceutical or therapeutic application.

22. The composition as defined in claim 17, wherein said pharmaceutical or therapeutic application is cancer therapy and disease treatment.

* * * * *